US007991485B2

(12) United States Patent
Zakim

(10) Patent No.: US 7,991,485 B2
(45) Date of Patent: *Aug. 2, 2011

(54) SYSTEM AND METHOD FOR OBTAINING, PROCESSING AND EVALUATING PATIENT INFORMATION FOR DIAGNOSING DISEASE AND SELECTING TREATMENT

(76) Inventor: David S. Zakim, Mill Valley, CA (US)

(*) Notice: Subject to any disclaimer, the term of this patent is extended or adjusted under 35 U.S.C. 154(b) by 912 days.

This patent is subject to a terminal disclaimer.

(21) Appl. No.: 11/933,185

(22) Filed: Oct. 31, 2007

(65) Prior Publication Data

US 2008/0177578 A1    Jul. 24, 2008

Related U.S. Application Data

(63) Continuation of application No. 09/522,792, filed on Mar. 10, 2000, now Pat. No. 7,379,885.

(51) Int. Cl.
*G06Q 10/00* (2006.01)
(52) U.S. Cl. ......................................................... 700/2
(58) Field of Classification Search .................... 705/2–3
See application file for complete search history.

(56) References Cited

U.S. PATENT DOCUMENTS

| 3,566,370 A | 2/1971 | Worthington et al. |
| 4,130,881 A | 12/1978 | Haessler et al. |
| 4,712,562 A | 12/1987 | Ohayon et al. |
| 4,838,275 A | 6/1989 | Lee |
| 5,012,411 A | 4/1991 | Policastro et al. |
| 5,235,510 A | 8/1993 | Yamada et al. |
| 5,544,044 A | 8/1996 | Leatherman |
| 5,622,171 A | 4/1997 | Asada et al. |
| 5,666,953 A | 9/1997 | Wilk |
| 5,687,716 A | 11/1997 | Kaufmann et al. |

(Continued)

FOREIGN PATENT DOCUMENTS

WO    WO-98/02836    1/1998

(Continued)

OTHER PUBLICATIONS

Long, W.J. et al.; "Differential Diagnosis Generation from a Causal Network with Possibilities,"; Computers in Cardiology, 1988, Washington, D.C., IEEE Comput. Soc. PR, pp. 185-188 (Sep. 1988).

(Continued)

*Primary Examiner* — Gerald J. O'Connor
*Assistant Examiner* — Minnah Seoh
(74) *Attorney, Agent, or Firm* — Wilmer Cutler Pickering Hale and Dorr LLP

(57) ABSTRACT

A computer-based system and method is disclosed which constructs medical histories by direct interactions between the patient and system that acquires pertinent and relevant medical information covering the complete life of a given patient. The system and method insure that a complete life long medical history is acquired from every patient interacting with the health care system. Once acquired, the facts of the patient's life long and family medical history are analyzed automatically by databases to generate a set of the most reasonable diagnostic possibilities (the differential diagnosis) for each medical problem identified and for each risk factor for disease that is uncovered in the historical database. Further, the automatically analyzed database of historical medical information is used as the search tool for bringing to bear, on the diagnosis and treatment of each medical problem identified in each patient, the entirety of medical knowledge that relates to and can be useful for the correct and efficient diagnosis and treatment of each of every patient's medical problems. This collection of information is analyzed to generate a final diagnosis and treatment regimen.

15 Claims, 4 Drawing Sheets

U.S. PATENT DOCUMENTS

| | | | |
|---|---|---|---|
| 5,823,948 | A | 10/1998 | Ross, Jr. et al. |
| 5,867,821 | A | 2/1999 | Ballantyne et al. |
| 5,868,699 | A | 2/1999 | Woodruff et al. |
| 5,897,493 | A | 4/1999 | Brown |
| 5,908,383 | A | 6/1999 | Brynjestad |
| 5,953,704 | A | 9/1999 | McIlroy et al. |
| 5,956,689 | A | 9/1999 | Everhart, III |
| 5,993,386 | A | 11/1999 | Ericsson |
| 6,000,828 | A | 12/1999 | Leet |
| 6,021,404 | A | 2/2000 | Moukheibir |
| 6,154,726 | A | 11/2000 | Rensimer et al. |
| 6,177,940 | B1 | 1/2001 | Bond et al. |
| 6,206,829 | B1 | 3/2001 | Iliff |
| 6,234,964 | B1 | 5/2001 | Iliff |
| 6,270,456 | B1 | 8/2001 | Iliff |
| 6,383,135 | B1 | 5/2002 | Chikovani et al. |
| 6,980,958 | B1 | 12/2005 | Surwit et al. |
| 7,379,885 | B1 | 5/2008 | Zakim |
| 2002/0107641 | A1 | 8/2002 | Schaeffer et al. |
| 2005/0177400 | A1 | 8/2005 | Rosenfeld et al. |

FOREIGN PATENT DOCUMENTS

| | | |
|---|---|---|
| WO | WO-01/69513 | 2/2001 |

OTHER PUBLICATIONS

Stetson, D. et al. "Structured Specification of a Computer-Assisted Medical Diagnostic System"; Proceedings of Third Annual IEEE Symposium on Computer-Based Medical Systems, (CAT. No. 90CH2845-6), Chapel Hill, NC, USA, Jun. 3-6, 1999.

International Search Report and Written Opinion of the International Searching Authority, the European Patent Office, for International Application No. PCT/US01/07339, dated Jul. 29, 2002, 6 pages.

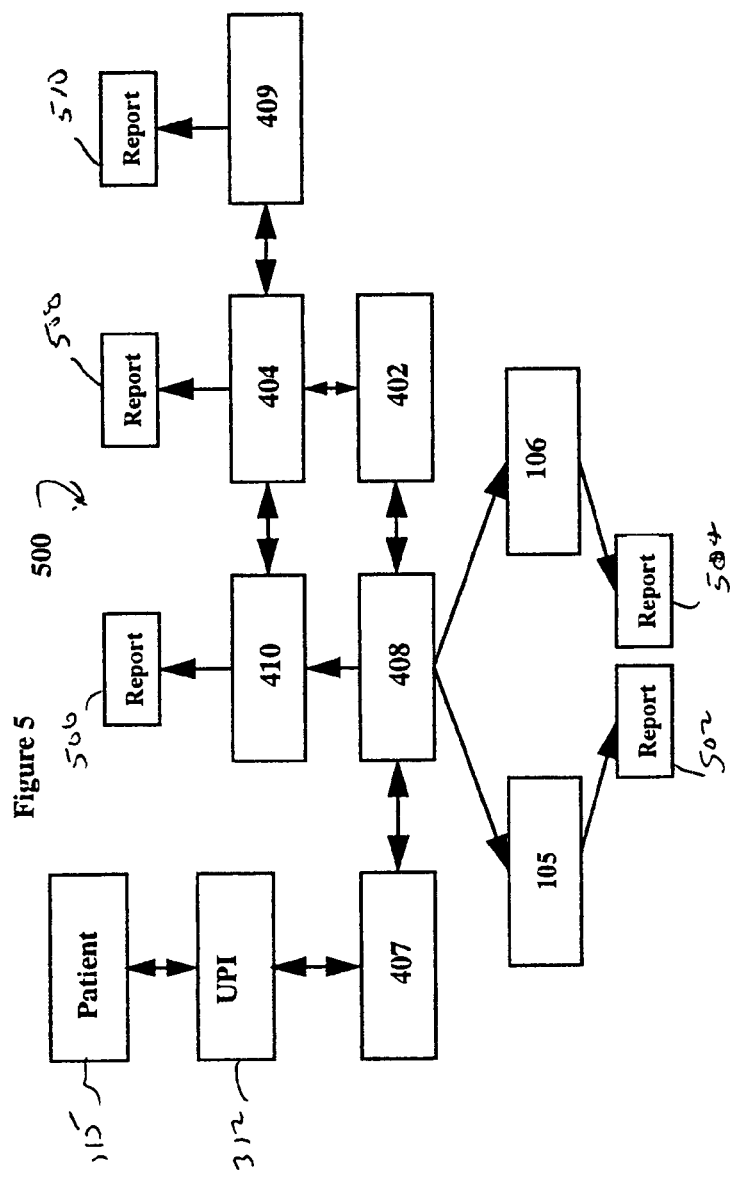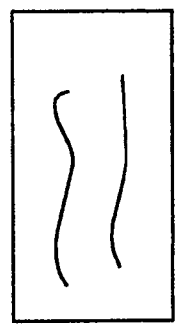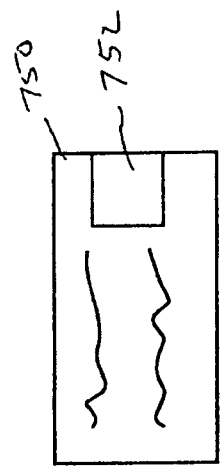

understand# SYSTEM AND METHOD FOR OBTAINING, PROCESSING AND EVALUATING PATIENT INFORMATION FOR DIAGNOSING DISEASE AND SELECTING TREATMENT

CROSS-REFERENCES TO RELATED APPLICATIONS

This application is a continuation of U.S. patent application Ser. No. 09/522,792, filed Mar. 10, 2000 and is incorporated by reference herein for all purposes.

FIELD OF THE INVENTION

The present invention relates to the system and method for obtaining, processing and evaluating patient data to generate a treatment or rule-based medical solution.

BACKGROUND TO THE INVENTION

The information age has provided many pluses with regard to the amount and quality of information available to everyone. This is especially true in the health care field because physicians and other health professionals now have access to large quantities of data on any subject in a short amount of time. However, attempts to access specific, desired information usually results in an unstructured "data dump" that is typically not responsive to these specific or specialized needs of the physician or health care professional. Taking the appropriate actions for a specific problem for a specific patient requires an ability to tailor this access to the vast amount of medical knowledge based on the specific medical needs of a particular patient. This type of tailoring, if it was available, would be of great help and would save time. More specifically, this tailoring would reduce the time needed to reach decisions about treatment and would improve the quality of medical care by insuring that physicians were always armed with the medical knowledge required to swiftly diagnosis and treat each specific medical problem of each patient.

The foregoing, if available, would result in an increase in the productivity of the health care system by making physicians and other facets thereof more responsive and efficient. It will also enhance the quality of care given to individual patients, and preserve, in a useful form, the work product of the health care system—the medical files of patients that have been treated.

Any increase in the efficiency of the health care system must take into account certain other factors. Examples of some of these are:

(i) the physician-patient relationship,
 (ii) the continuing medical education of physicians,
 (iii) the rapid introduction into clinical practice of advances in knowledge about disease,
 (iv) the rapid deployment of newly approved medications,
 (v) the reduction of medical liability costs,
 (vi) the reduction in the practice of "defensive medicine,"
 (vii) the planning and execution of medical research,
 (viii) the monitoring of medical practice habits,
 (ix) patient education and treatment compliance,
 (x) preventive medicine to reduce morbidity, and
 (xi) the cost of health care.

The considerations referred to above will require re-engineering of the current health care system to increase its efficiency. When this is done, it will overcome the endemic problems in the system which have been the widely acknowledged to include: high and escalating costs of health care in the United States and worldwide and lack of a uniform quality of care in all areas where health care is administered. There also are serious problems in the ability of the health care system to address emerging issues in health care in more than a purely localized way.

Physicians, for example, are under pressure to increase the number of patients that they see and also reduce the time spent with each, individual patient. This, among other things, results in an erosion in the physician-patient relationship. This, in-part, is based on physicians having little time to assess patient needs, develop the most correct and efficient plans for treatment, or establish a rapport with the patient.

A review of typical medical practice habits indicates that "patient history taking" suffers most when stringent time constraints are put on physicians or other health care professionals. On the other hand, a time-intensive process, such as this, is needed now more than ever, given the efficacy of drugs and physical actions for prolonging not only life but the quality of life.

"Patient history taking" has been a constant in the practice of medicine. This procedure requires more of the physician's time than any other aspect of physician-patient interaction. In most cases, physicians are not remunerated at fair value for the time spent with patients in "patient history taking." For example, in "health maintenance organizations" ("HMOs"), a physician's remuneration is tied directly to the numbers of patients seen and number of procedures performed rather than the time, effort, and quality of the medical care provided. This approach is unfortunate and dangerous given that the "patient medical history" is the single most important event of the physician-patient interaction. Experience has shown that when a thorough "patient medical history" is taken, a correct diagnosis can be made, in at least 80% of patients. The patient's medical history, therefore, is of paramount importance to physicians for making efficient, rational medical care decisions.

Another important facet of the physician-patient interaction that suffers when physicians have less time to spend with patients is the reduction in the information that patients learn about their disease. This will include the nature of their disease, the importance of treatment compliance, and patient activities that can control the outcome of their illness, to name a few.

The current health care environment requires alternative methods for obtaining and maintaining a patient's complete medical history, reading and evaluating the information in a medical history (which may be in the form of check-off forms completed by patients), and educating patients about their illnesses. These alternative methods have been needed long before now and they were even needed during times when "fee for service medicine" was apparently at its height. Since physicians are best suited to understand a patient's medical history and other medically relevant facts, these alternative methods have not been, and continues not to be, implemented because they would be administered by lay people, not physicians.

The development of a proper patient history follows a logical process based on extensive knowledge of clinical medicine, physiology, and pathophysiology. It is not, as many non-physicians believe, merely a compilation of data amassed through the use of check-off forms or by a scribe. Accordingly, methods are needed to obtain and maintain a patient's full history while holding down costs.

The present health care system lacks the ability to keep physicians up-to-date with respect to the latest developments in medical science. This includes developments in disease diagnosis and treatment in highly specific instances. Many disparate factors contribute to this problem. A first is that the number of new methods for diagnosis and treatment of disease is expanding at exponential rates. This wealth of new and innovative diagnosis and treatment procedures, along with the wealth of existing knowledge, however, create of formidable challenge for physicians if they attempt to master it. This is particularly true since the formal period of medical education, i.e., medical school, internship, and residency training, is decreasing and a large number of practicing physicians do not have ready access to the information.

This problem is not solved merely by increasing the formal aspects of medical education. Even if this was done, physicians would not have the needed information because the range of knowledge and experience required to practice state-of-the-art medicine increases daily. Moreover, the obsolescence of medical information is so rapid that the information that a physician learned in formal medical training a short time before is often no longer state-of-the-art medicine. No one physician can know and recall on demand more than a small portion of the total wealth of medical knowledge that applies to a specific disease. It does not matter how intelligent or knowledgeable the physician; there will be a gap between a particular physician's knowledge and a real state of medical knowledge.

High quality patient care increasingly relies on a physician knowing the very specific details about particular diseases and the treatment regimens for such diseases. This includes knowledge of, and familiarity with, what is known by highly trained sub-specialists in the different fields of medicine. It also may be directed to areas in which a particular physician has gained little or limited expertise during his or her medical training. These are diametrically opposed issues in health care for physicians. Accordingly, physicians must: (i) find a way to have full knowledge of established, and new and innovative diagnosis and treatment procedures and (ii) obtain this knowledge with less time to do it. The present health care system, however, charges ahead without a solution to these problems believing that physicians with less training and expertise will still be able to provide high quality care.

The seemingly daily advances in medical research have created for physicians unprecedented opportunities to have a positive impact on the lives of their patients. There are serious problems in physicians availing themselves of this new information in a manner in which they can immediately impact the care of their patients. Because of this problem, there is a widening gap between the knowledge physicians possess and the information that is actually available. This means the losers are the patients.

There is ample evidence for this gap. For example, common diseases, e.g., diabetes, abnormalities of blood lipids (that predispose to heart disease), and high blood pressure, are often under treated or not treated at all. This is because the physician does not know the most current or even the complete methods for the accurate diagnosis and treatment of the patient's conditions. This reflects the physician's lack of experience and his/her lack of continuing educational training in managing diseases. This difficulty in keeping practicing physicians fully informed is becoming more acute with each passing day because of their inability to know of and prescribe new drugs or understand how to use new procedures.

The "knowledge gap" can only be narrowed through continuing medical education ("CME"). Current methods for CME are abstract and usually not relevant to the specific, immediate needs physicians have in caring for their specific patients. CME, as it is administered now, requires large amounts of physician time outside of the clinically productive environment in which physicians work. Moreover, it is expensive. Today's CME programs are narrow in scope and focus, and ineffective in addressing the knowledge gap. Even when CME is considered effective, it does not solve a physician's almost impossible task of recalling selective pieces of information he or she receives. As such, it is not readily available for diagnosis and treatment of a diverse array of patients.

Another problem with the current state of the health care system is the in which medical records are kept and transferred from physician to physician (when needed). The health care system as we know it has no way of extracting important and needed knowledge from one of its most important work products, which is: the records of all patients who are treated. That is, millions of patients are treated and cared for each year, but the demographics, epidemiology, and records of patients' diseases, as well as the outcomes from treatment, are kept in a form that prevents general use of this information.

On Aug. 4, 1999, The NY Times® ("Times") is a registered trademark of _____) reported that the health care system in effect was not using the information with which it is imbued in an effective way. The Times article cited a study showing that treatment with Ritalin did not lead to higher subsequent rates of drug abuse in male patients, as previously believed. The conclusion that Ritalin had no adverse effect on the subsequent incidences of drug abuse was based on results from only 75 patients. The article also indicated that approximately 1.5 million male patients were taking Ritalin in the United States. It, however, did not comment on the sample error that is the result of only a 75 patient sample set and the non-inclusion of the remaining 99.995% of the total number of men that could have been part of the survey. The reason that no more than 75 patients were part of the sample set is the manner in which medical records are acquired and maintained. This problem made it next to impossible to obtain relevant data from the remaining 1,499,925 patients that were not included in the Ritalin study.

A yet further problem of the current health care system is its inability to prevent the serious complications of disease processes by the early identification of people who are affected prior to the onset of these complications. The key to solving this problem is having adequate resources to conduct population surveys of healthy people to find evidence of incipient disease. Since collective records of such patients are not available, the costs of such population surveys, if they could be done at all, would require a great deal of physician time—time that physicians do not have.

There have been attempts to solve some of the problems discussed. There have been computer-based methods for acquiring medical histories from patients. These systems diagnose disease under limited circumstances. For example, U.S. Pat. No. 4,130,881 discloses that a patient's medical history can be acquired and recorded using computer technology. This system, however, does not provide any method for the interpretation of the historical data, guidelines for the further evaluation of the historical data, easy incorporation of advances in knowledge, and or the like.

Further, U.S. Pat. Nos. 4,7,12,562, 4,838,275, and 5,012,411 use computers in a different way than U.S. Pat. No. 4,130,881. The systems described in the '562, '275, and '411 patents use computers for interpreting and analyzing physiologic data acquired by electronic monitoring of a patient. This interpretation and analysis is directed to rudimentary types of measurements, such as heart rate and blood pressure, for the purpose of treating blood pressure.

Another computer-based system is described in U.S. Pat. No. 5,868,699 and other patents by its inventor, Illiff. The '699 patent is directed to systems that use a computer to implement an expert system to provide a diagnosis based on a patient's medical history. These systems are of the type for providing patients with guidance to determine if he/she should seek medical advice. The data upon which these systems rely is based on an analysis of symptom complexes associated with the 100 most common complaints that patients have in the United States. The diagnoses that are provided are based on several assumptions about the practice of medicine. These assumptions include:

(i) that the method for diagnosis from an historical data base does not change, (ii) that disease entities that represent the 100 most common symptom complexes are singular, (iii) that accurate diagnoses can be made from historical data alone or with data from a patient's self examination, (iv) that face-to-face interactions between patient and physician add no value to the diagnosis of disease, and (v) that patients can determine the best treatment for their disease from tabulated arrays of diagnoses and drugs.

The history component of the current invention is not based on these or any other assumptions.

The system described in the '699 patent and other patents by inventor Illiff require expert input from the patient in the form of conclusions as to the organ causing symptoms. Alternatively, when the patient (the user) cannot provide such expert input, these patents disclose that the user is asked for his or her expert conclusion as to the cause of the symptoms.

The '699 patent and other patents by inventor Illiff also require that the user fill out questionnaires. These questionnaires are transmitted to the patient by facsimile or mailed for the purpose of completing relevant historical facts omitted during the initial, computer-based interrogation of the patient. These two sets of information eventually form the basis of a patient's medical history.

The '699 and other patents by inventor Illiff depend on the knowledge, training, and skill of a computer programmer for investigating specific answers to any and all questions in a patient's history. The prior art specified by inventor Illiff makes important assumptions during the collection of data for the history which may result in an incomplete medical history for diagnosing disease, i.e., the assumption that some types of information have importance and other types does not with regard to the immediate problem.

U.S. Pat. Nos. 3,566370 and 4,130,881 describe systems that use a computer to acquire information for a patient's medical history. These patents are directed only to this limited task. These patents do not state the purposes for acquiring the histories except for review by a physician or other health care provider. In the '370 and '881 patents, the patients have to select for themselves, whether they are using the medical history facility for the first time (for an initial history) or for a subsequent time (for a follow-up history). Moreover, in the limited aspect of acquiring a medical history, the '370 and '881 patents describe methods that depend on the patient's ability to discern the organ that is the site of their disorder or discomfort.

Lastly, the medical histories, according to the '370 and '881 patents, require that the entire history that is collected be read and interpreted by the physician or any other person intending to render care to a patient.

U.S. Pat. No. 5,666,953 describes a method for collecting and digitizing data acquired by a monitoring device attached to a patient. U.S. Pat. No. 5,897,493 discloses a system to monitor patients with chronic diseases at home using devices that might for example monitor blood sugar in a diabetic. The peripheral monitor is connected to a central computer, which might query the patient depending on the value of the blood sugar. The system in the '493 patent is limited to a single disease entity per patient or peripheral device. It is limited to chronic diseases with features susceptible to monitoring by peripheral devices attached to a patient. It is not open to inputs outside the strict limits of the input from the peripheral monitoring device and associated built-in questions. Further, it does not include a method for exploring the presence or absence of disease outside the limits of the monitored system nor does it have diagnostic features. The system of the '493 patent has no educational features outside the limited area of the monitoring device and does not have features for building databases for the purpose of clinical research across a broad array of diseases. Finally, the system does not automatically notify doctors or patients of changes in the state of art informing the practice of medicine in any area of medicine.

U.S. Pat. No. 5,235,510 discloses a method for collecting and digitizing imaging data, e.g., an MRI scan and a CAT scan. The method then using a computer to analyze and interpret the medically relevant data. The method described in the '510 patent digitizes image data to provide medically relevant interpretations of such digitized images.

U.S. Pat. No. 5,687,716 describes a computer-based method that uses statistical methods to diagnose a patient's medical problem. The system of the '716 patent is limited to the analysis of parameters that are obtained by clinical testing and converted to numerical expressions. According to the '716 patent, any type of statistical method, including neural network analysis of a database of laboratory results, can be used to search for a deeper meaning in the data than might be apparent from a physician's interpretation of the same data. The method of the '716 patent operates under the assumption that patients can be separated, for this purpose, into those considered normal and those for which the analysis indicates the presence of disease. The analysis described in the '716 patent is the basis by which that system operates to enhance the productivity of the medical care system or to improve its quality. The method in the '716 patent does not interact directly with the patient to acquire historical data. Nor does it interpret laboratory data in the total context of all other clinical data.

U.S. Pat. No. 5,544,044 discloses a method for computer-based analysis of health claims forms in order to evaluate the quality of care received by a given set of patients, enrolled in a specific health plan, with a specific, given illness. The method of the '044 patent is severely limited in its capacity to estimate the quality of health care rendered. The system of the '044 patent has the ability to examine health care only at a single instant in time and it can do this only after health care has been rendered. There are no other uses described for this invention. The system described in the '044 patent operates based on the assumption, which is programmed into its analytic algorithm, that all patient's with the same, given coded diagnosis have identical medical profiles. This analysis of medical records or health claims files is inherently incorrect and can lead to faulty conclusions about the quality if care being rendered.

The present invention overcomes the problems set forth above as will be described in the remainder of the specification referring to the drawings.

SUMMARY OF THE INVENTION

The present invention is centrally deployed, computer-based system and method that may be coupled with analytic systems and databases. This system and method use a global communication system, e.g., the Internet, to acquire, analyze, and store all medically relevant facts about all patients interacting with the system. The central deployed, computer-based system of the present invention has various components that will increase the efficiency of the health care system while also improving the quality of care to individual patients.

The system and method of the present invention relieve the physicians of the tasks of acquiring and writing down complete medical histories and to some degree educating patients about their illnesses. The present invention provides for the efficient flow of clinically relevant information from clinical and basic science research to clinical use in the care of specific patients. This enhancement is effected by the rapid deployment of newly introduced medications into widespread clinical practice. The present invention also provides for rapid and confidential access to the complete medical records of any patient using the system. This will include the use of access control Smart Card-type technology for the control, transport, to and transfer of patient's medical history records.

Further, the present invention provides a system and method that has the capability to reconstruct in exact chronological detail the medical history of any enrolled patient, yet also control access to the identity of that patient. As such, there is the realization of complete patient files being available as a new tool for clinical research without compromising the identity of individual patients. This can be very helpful in clinical research because these files may have varied uses for determining the outcome of specific diseases. They also may be useful for the identification of new uses for already deployed medications, or the identification of patients who are candidates for important clinical studies.

The present invention also represents a new and novel system and method for the continuing education of physicians and patients so that detailed knowledge about disease may be acquired or accessed in real-time for the efficient treatment of patients. Accordingly, educational material is provided on an individualized basis for each specific clinical problem for each patient in a physician's practice. This educational material is keyed to a patient's specific medical problems and is delivered to the physician in the immediate clinical setting. The educational material is in the form of a continuous stream of relevant medical information that is dynamic to keep pace with the changing nature of a patient's medical condition.

The present invention includes, as a component, an expert system that uses the data entered into the patient's database to automatically and continuously compare the efficacy of treatment in each patient versus goals for treatment in patients with similar diseases and detailed disease profiles. Therefore, as changes occur in the data, there will be appropriate changes and recommendations to the physician so that better treatment regimens may be provided to the patient.

The present invention provides a convenient and inexpensive method for communications between patients and physicians on a day-to-day basis. This will continually give physicians the necessary information before seeing a patient to determine whether changes in the treatment regimen are needed and whether additional diagnostic tests are warranted. As such, physicians can track the course of disease in patients on a day-to-day basis without the necessity to examine or question the patient directly.

The system of the present invention includes the use of system generated databases for determining the significance of newly formed clinically relevant questions through analysis of, and comparisons with, data from millions of patients. For example, while it is known that the risk of thromboembolism in all women taking oral contraceptives is no higher than the risk in women not taking oral contraceptives, a remaining uncertainty is whether there are subclasses of women with greater than average risk for thromboembolic events while taking oral contraceptives. The data for resolving who is at risk in a subset of women may be determined by examining and analyzing the history of outcomes over years for all women taking oral contraceptives. This data was once available but now is lost for the lack of a method to acquire the data in an automated manner and to store it in a manner that makes it easily accessible and subject to analysis. Heretofore, such analysis, though only partial, could only be done by a costly, multi-year prospective clinical study that would attempt to recreate the data that has been lost. Doing such a study with current technology would, however, yield results that would be less than comprehensive because data would be available for relatively few women. Further, results would not be available for years to come.

The present invention provides a method and system for studying an entire population at risk in a real-time, real-world setting in which patients at risk live and are treated. This differs from conventional methods that consist of the highly controlled, idealized settings of clinical research trials. The present invention automatically enrolls and tracks all patients in prospective clinical research studies relevant to the specifics of their diseases and treatments. This can be done at no added cost to the medical care system.

The system and method of the present invention are capable of determining the incidences of different diseases across populations on a country-wide or worldwide basis, and rapidly assessing changes in such trends. This is in contrast to what is shown in the '699 patent. Also, the history component in the '699 patent is interpreted for use by the patient. The history component of the present invention in contrast, provides the physician with patient-specific educational materials based on an automated analysis of the patient's history, e.g., the contents of the patient's history. The history component of the present invention is not intended for use by patients but by the physician. This history component does not allow patients to practice medicine on themselves. The system of the present invention is designed to add value to the traditional physician-patient interaction not to substitute for it.

The system and method of the present invention also solve the problem associated with gathering large amounts of follow-up data on patients taking newly introduced medications, which is a clear weakness of the current system for delivering health care.

The medical history that is taken according to the present invention is akin to one taken by an expert physician. The medical history asks questions—in logical sequence—while addressing a patient. The present invention simulates the logical processes of the ideal physician armed with an complete and up-to-date knowledge of the disease, disease processes, and methods of diagnosis and treatment as these apply to all possible medical diagnoses and in all branches of medicine. The methods used by physicians to obtain and interpret historical data continuously during interview of a patient are constructed automatically by the system's history component.

The history component of the present invention is structured on the basis that all medical information will be relevant to the patient's health and it is potentially dangerous to make arbitrary decisions as to what is important. The history component of the present invention is not limited in its analytical ability to any limited number of diseases or sets of symptom complexes.

The system and method of the present invention, are further distinguishing from current and known system by the following:

The physician or physician's assistants can directly access specific answers to specific questions in any part of a patient's medical history. This may be done any time after the history component has acquired data from a patient. No computer expert is required as an intermediary for this process. Additionally, in the history component of the present invention, all answers to all questions can be printed out in hard copy so that no computer skills are required to access any part of the medically relevant information stored in the history component.

Acquisition of a medical history is one component of the present invention. The present invention describes several ways in which the data acquired in the form of a medical history can be used on-line to increase the productivity of the health care system, to improve the quality of care, and to enhance the education of physicians.

The present invention includes a universal patient interface ("UPI"). It is through use of the UPI that medical history information is acquired. It is also through use of the UPI that information is gathered and a determination may be made, for example, of the organ causing the patient's problem.

The system and method of the present invention, automatically determines whether the patient is to provide an initial or a follow-up history. The present invention contains analytic components that provide the physician with a medical analysis of a patient's history to indicate the specific medical issues and risk factors for disease that have been identified.

The present invention describes a system that has the ability to integrate the medical data obtained during an initial visit with the medical history, e.g., the physical examination, obtained for subsequent follow-up visits for a given patient and/or with any laboratory test that is performed on the patient. The present invention also has the ability to integrate other medical data besides the medical history with the medical data obtained at an initial visit and with the medical history obtained for subsequent follow-up visits for a given patient.

Further, the present invention allows for updating the programs that acquire the medical history as changes occur in the fundamental base of knowledge that improves the practice of medicine. The present invention provides the patient with an understanding of the risk factors identified by the acquisition of the history over which the patient has control.

The present invention automatically incorporates and integrates collected data in the patient's complete database. This includes, but is not limited to, an initial history, follow-up history, response to treatment or lack thereof, all other laboratory data, and automatically analyzing any data acquired in the full context of the complete medical history and all laboratory data.

The present invention has the ability to store images and their medically relevant interpretations as isolated facts. The present invention also automatically integrates the findings derived from data into the patient's complete medical database that includes, but is not limited to, an initial history, follow-up history, response to treatment or lack thereof, all other laboratory data, and automatically analyzing any data acquired in the full context of the complete medical history and all laboratory data.

The present invention describes a system that enforces interpretation of medically relevant images to conform to medically accepted norms determined by experts in the field. The purpose of this is to make the interpretations immediately understandable and useful to any physician or appropriate health care professional seeking to use them, for the diagnosis and treatment of a patient, without the need for re-review of the images. Further, the present invention, forces standardized interpretations of imaging data so that the diagnostic interpretation of an image has an exact meaning for any practitioner using the result for the purpose of diagnosis, prognosis, and/or treatment.

The present invention makes no assumptions in order to analyze the significance of any feature in the database.

The basic analytic systems of the present invention are not limited to data acquired by clinical testing, that is numeric, or that is analyzed by statistical methods. Additionally, the application of statistical methods to analysis of the databases generated by the present invention is not limited to data that is acquired by clinical testing or that is numerical in nature.

The present invention can examine and determine the quality of health care rendered across the entire lifetime of the patient. The present invention has a mechanism by which the quality of health care rendered to any single patient can be monitored at any point in time or continuously during the course of treatment.

The present invention has a mechanism by which the examination of the quality of health care rendered to any single patient can be used to alter the current course of treatment being rendered to the specific patient for whom the review was made. Moreover, the present invention has another mechanism by which the examination of the quality of health care rendered to any single patient can be used to determine whether poor quality care reflects errors in the diagnosis of the patient's disease, errors due to incomplete diagnosis of the patient's condition, or errors in treatment of the patient's condition.

Yet further, the present invention has a mechanism by which the examination of the quality of health care rendered to any single patient can be used to determine whether a poor outcome reflects errors by the physician or lack of compliance by the patient. The present invention has a mechanism by which the examination of the quality of health care rendered to any single patient can be conducted on currently active medical records. Another mechanism of the present invention is that medical records of patients with a given medical condition or constellation of conditions can be searched specifically on-line to examine the quality of care rendered.

The present invention assesses quality of care issues without assuming that all patients with the same, given coded diagnosis have identical medical profiles. The present invention has an on-line mechanism by which the examination of the quality of health care rendered leads to specific, real-time remedial education programs for physicians and patients. Moreover, the present invention has a mechanism by which the examination of the quality of health care can occur on-line and by which databases can be examined on a practice by practice basis.

The system and method of the present invention will describe in greater detail in the remainder of the specification referring to the drawings.

BRIEF DESCRIPTION OF THE DRAWINGS

FIG. 5 is a diagram that shows the reporting system for the present invention.

FIG. 6 is a system access card of the present invention.

FIG. 7 is a system control and storage card of the present invention.

DETAILED DESCRIPTION OF THE INVENTION

The present invention is a computer-based system and method by which physicians (and other health professionals) and patients interact to construct medical histories of each patients in a timely manner and then analyze the medical histories with respect to patient medical histories of other system subscribers. This analysis will aid in the diagnosis and treatment of a patient. The present invention also entails providing physicians with up-to-date materials in real-time for the diagnosis and treatment of disease based on the analysis of a particular patient's medical history that has been compared to information stored in system databases. Further, the present invention provides a system and method that securely stores the medical history information of system subscribers but makes this information available in an anonymous manner to physicians for analysis for the purposes of clinical research. The present invention further provides a system and method that may use Smart Card-type technology to control access to the identity of a patient to whom a particular medical history information relates and provides the patient with the ability to control which physicians will be able to relate particular medical history information with that patient when such a patient desires to transfer care from on physician to another.

Figure 1:
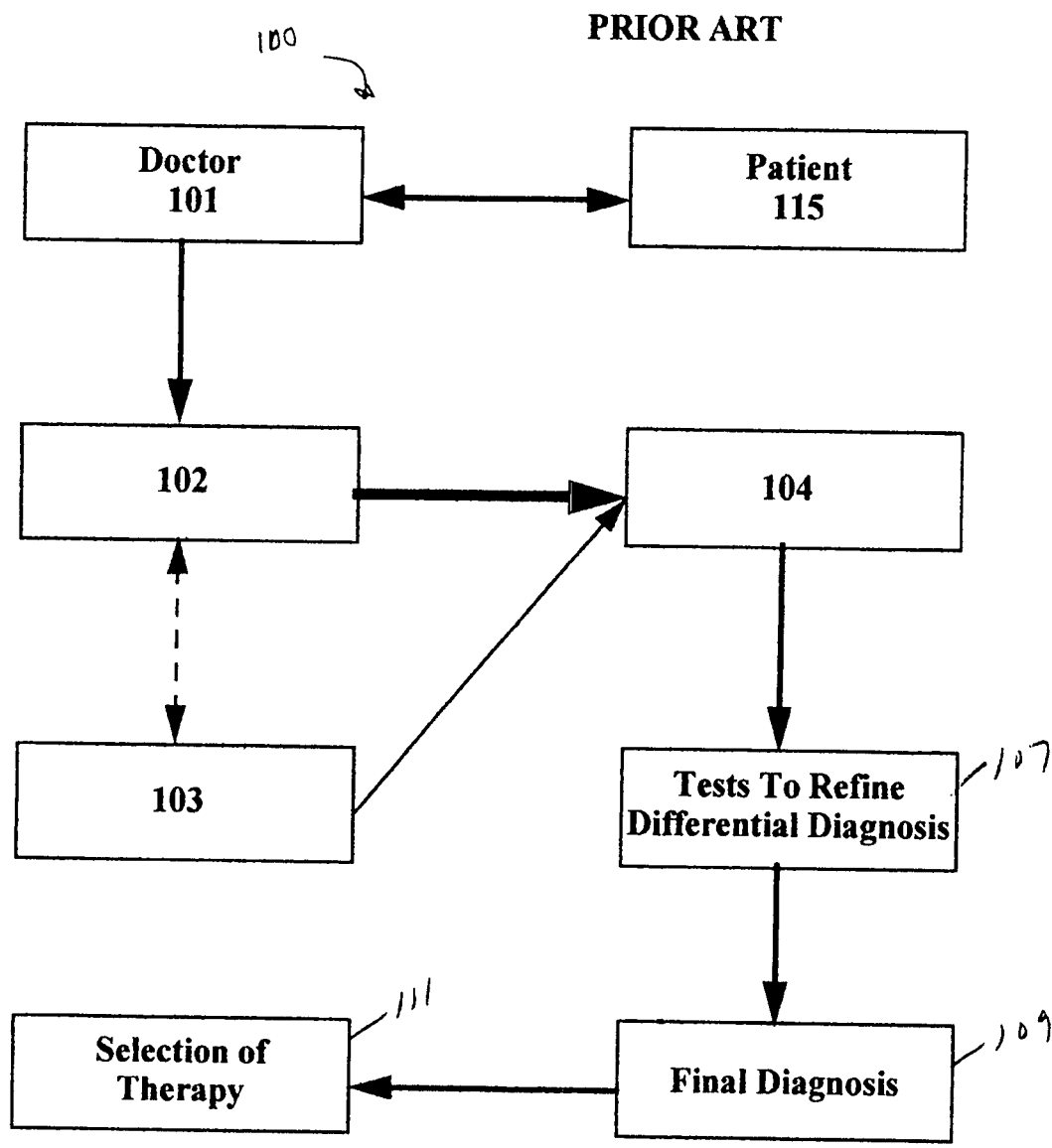
FIG. 1 is a schematic representation of the traditional method of the practice of medicine that leads to disease diagnosis and the selection of a treatment.

FIG. 1 is a schematic representation of the prior art method practicing medicine. FIG. 1, generally at 100, shows the flow of information that leads the physician to a diagnosis and selection of treatment. The relative thickness of the arrows in the representation indicates the amount and value of information in the context of making a diagnosis. For example, completely accurate diagnoses can be made 80% of the time on the basis only on the history in database 102, assuming that the information used to construct database 102 is complete.

Now referring generally to FIG. 1, at 100, doctor 101, at the outset, knows nothing or little about the patient until the time a medical history is acquired. Doctor 101 uses his/her immediately accessible knowledge of medicine and clinical experience in his/her mental database to collect a rules-based history of the medically significant events in the life of patient 115 up to the time of the their first meeting. Doctor 101 attempts to fill in the medical details of patient 115's complaint(s) and past life to generate database 102. Database 102 will contain the history of the patient's illness, past illnesses, if any, family history, and evidence of the risk factors for disease that occur because of the patient's life style, e.g., smoking. After collecting the information for database 102, the doctor proceeds to collect information for database 103. Database 103 will contain information relevant to the evidence of disease and lack thereof gathered from a physical examination of the patient. The directions for collecting the information for database 103 come from information database 102. For example, the information in database 102 may be suggestive of heart disease but not neurological disease. In such a case, the doctor might emphasize collection of data about the heart as he/she acquires the information for database 103. By contrast, if the information in database 102 suggests that a neurologic problem is the basis for the patient's complaints, then the doctor might emphasize collection of information about the neurologic system versus the heart when acquiring information for database 103. In either case, the combination of information in 102 and 103 is interpreted by doctor 101 to generate database 104. Database 104 will be a list of the diagnostic possibilities that could account for all the facts in databases 102 and 103. Once doctor 101 has generated database 104, he/she may choose certain tests to refine the differential diagnosis at 107. These tests will then permit doctor 101 to reach the final diagnosis at 109. Once the final diagnosis is known, then doctor 101 will select the proper therapy at 111.

As stated, FIG. 1 shows medical practice as it is currently constituted. It relies on the medical expertise and clinical experience of a single physician for the purpose of acquiring and analyzing a patient's medical history, for making diagnoses, and for selecting treatments. This means that the quality medical care will depend on a match between the information that the doctor 101 knows and the up-to-date body of medical information that may apply to the diagnosis and treatment of any problem occurring in any patient in a physician's practice. It is well known, however, that medical expertise and clinical experience are highly variable from one physician to another. As such, the quality and completeness of different key features of health care do not always, or may never, reach the quality attainable if physicians were able to use the most current and correct medical knowledge available for history taking, analysis of historical and other medical information (for making diagnoses correctly and efficiently, and for selecting the most helpful treatments for patients). It is estimated, for example, that most of the adverse reactions to prescription drugs in the United States could be avoided if physicians took the time and care, and/or had the relevant knowledge to acquire more complete and clinically pertinent medical histories from their patients.

Figure 2:
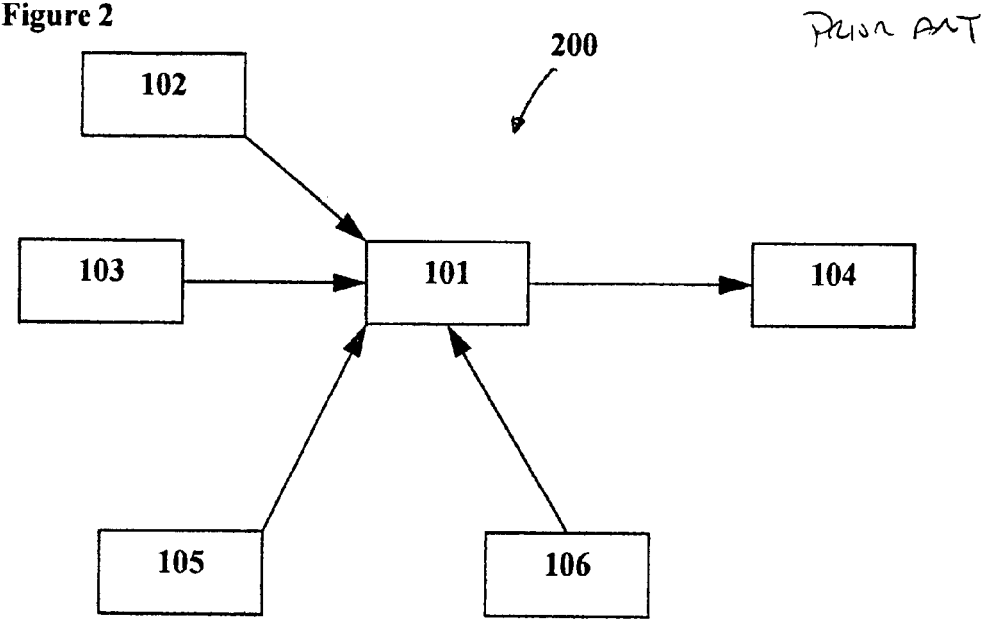
FIG. 2 is a schematic representation of the traditional method by which physicians acquire knowledge.

Referring to FIG. 2, generally at 200, a diagram is shown which could assist the physician in reaching a diagnosis and treatment. Doctor 101 could bolster his/her knowledge of medicine after acquiring databases 102 and 103. This would assist in generating the differential diagnosis database 104. This may be done by obtaining information from consulting databases 105 and 106. Database 105 represents the body of well established medical knowledge and database 106 represents, for example, 4,000,000 medical journal articles published each year. Under the present health care system, it is extremely expensive to acquire the information from databases 105 and 106, and be able to use it in a meaningful way. Moreover, a great deal of time is needed to read and digest the information in these databases and a physician endeavoring to do this would not be compensated for his/her time.

Databases 105 and 106 are vast. A single individual, even using computer searches, cannot search them efficiently. Searching databases 105 and/or 106, using any input as the search tool, will produce an incredibly large number of hits. Each of these hits must be read to determine whether they provide information useful for the diagnosis and treatment of a specific problem in a specific patient. Since this cannot be done in the real-time setting of the doctor-patient interaction, or even in a proximate time setting, the full value of information obtained from searching databases 105 and/or 106 will have to be remembered and then recalled by the doctor when the patient, for whom a search was made, returns to the doctor's office.

Medicine may be practiced effectively according to the methods set forth in FIGS. 1 and 2, as long as, there is a relatively small amounts of information that will apply to the large array of clinical problems occurring in the population of patients that make up any single physician's medical practice. Medical progress, however, makes it increasingly difficult for any physician, whether generalist or specialist, to know more than a small fraction of the medical knowledge relevant to a doctor's specific area of practice. It is physically impossible for a physician to know what's in all of the world's medical libraries and what new appears each day. Even if this material were knowable, it would be physically impossible to have immediate recall of just the right package of information for each specific clinical situation across an array of patients. The result for patients is that most, if not all, are subject to medical care that is less well informed compared to the state of medical knowledge pertaining to the specific problems in specific patients at any given point in time. Because the medical knowledge information base is so large and expanding rapidly, there are gaps between what any given physician knows and/or remembers about the details of any given medical problem or procedure, and the state of medical knowledge applicable to that specific problem. This short-coming is avoidable.

Figure 3:
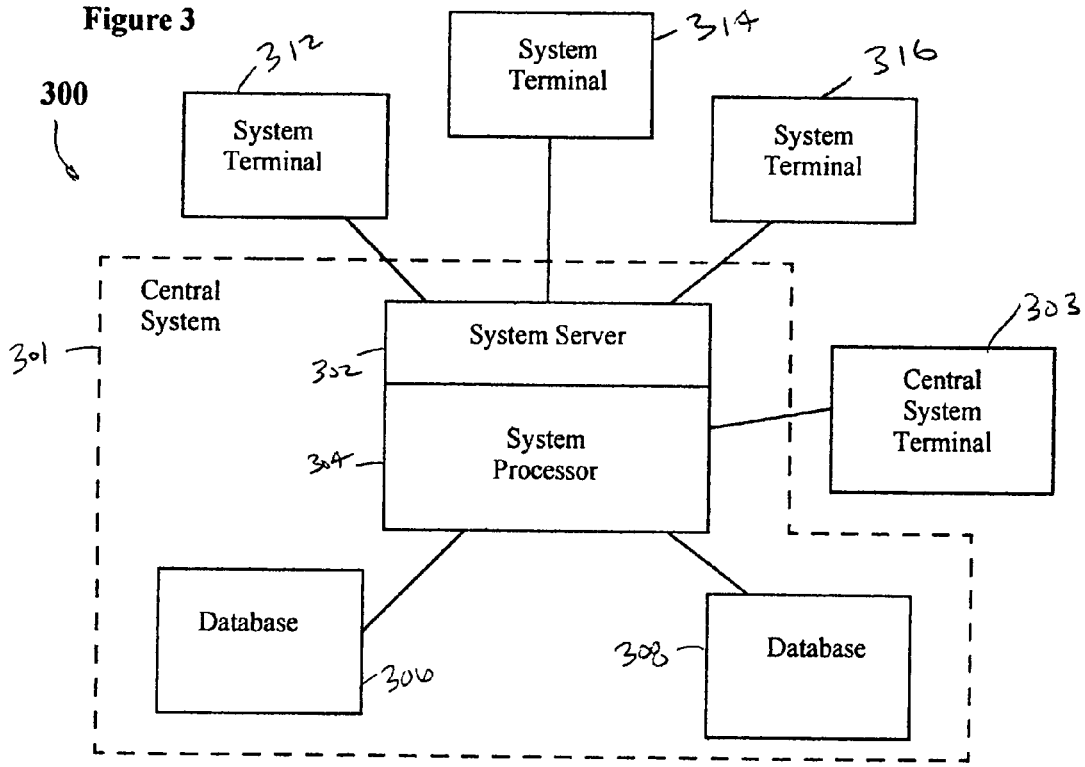
FIG. 3 is a block diagram of the system of the present invention.

FIG. 3, at 300, shows a block diagram of the system of the present invention. The system may be implemented in a large area network ("LAN"), a wide area network ("WAN"), a metropolitan area network ("MAN") or an Internet-based system. The system includes system server 302, which serves as the connection point for system subscribers. System processor 304 connects to system server 302. The system processor includes system programming and security recognition technology systems.

Figure 4:
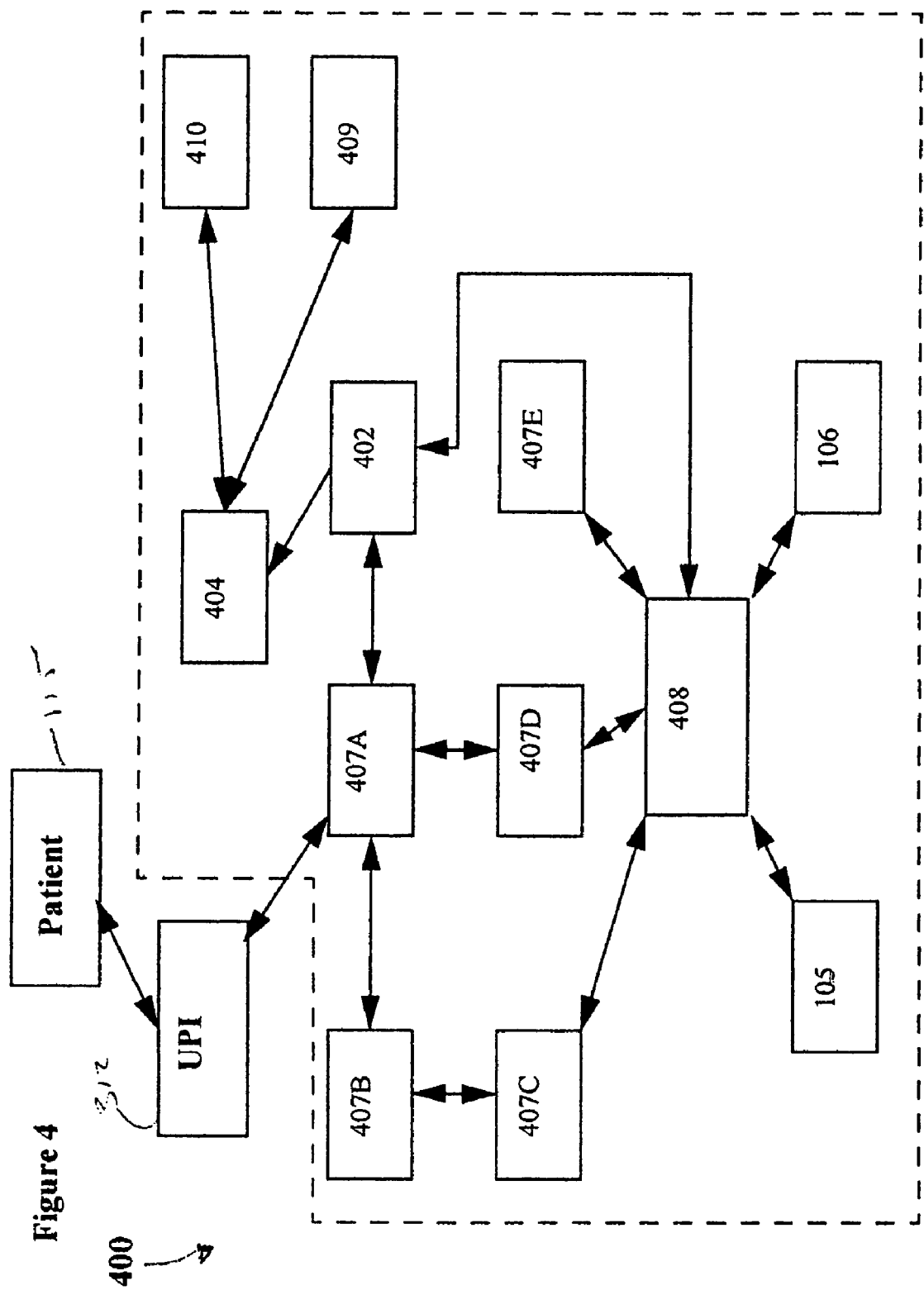
FIG. 4 is a diagram of the operation of central system in FIG. 3.

Central databases 306 and 308 connect to system processor 304. For example, central database 306 could store the medical histories of all system patients and central database 308 could include educational information relating to the diagnosis and treatment for various diseases, sicknesses, and other medical problems. It is also understood that these databases are representative of the system databases and that such databases may contain other types or categories of information and still be within the scope of the present invention. For example, central database 308 may contain the information in databases 105 and 106 (FIGS. 4 and 5). Further, central database 306 may contain the information in databases 402, 404, 407, 408, 409, and 410 (FIGS. 4 and 5).

Central system terminal 303 connects to system processor 304. Central system terminal 303 is used for performing system diagnostics and inputting information to, and removing information from, the system databases. The central system terminal may be connected to separate feeds to obtain recent information for the databases, such as feeds from a laboratory.

System server 302, system processor 304, central system terminal 303, and central databases 306 and 308 form central system 301 of the present invention. It is understood that the present invention may have the central system that is configured differently and still be within the scope of the present invention. For example, the central system may have two or more servers that are separated that are interconnected, a plurality of processors for carrying out discrete functions, one or more than three databases, include different types of memory structures, e.g., cache memories, or connected peripherals.

Again referring to FIG. 3, system terminals 312, 314, and 316 are shown. These terminals may be used by physicians or other qualified personnel to input data to, or retrieve information from, the system databases. These terminals also may be used by patients to input or retrieve information. A terminal may be located at a physician's office or other appropriate site where patient medical history information may be obtained or where a physician would desire to obtain educational information from the diagnosis and treatment of patients. These terminals also may be located where they are accessible by patients.

System terminals 312, 314, and 316 connect to system server 302. It is understood that the system of the present invention may include more or less than three system terminals and still be within the scope of the present invention.

The medical history information for a patient may be entered into the system in a number of ways. For example, it may be entered in-part by the patient or entered by the physician. Non-historical but medically relevant data may be entered by physicians and laboratories. It may be entered directly into the system of the present invention as shown in FIG. 3 through terminals 312, 314, or 316, or placed on a CD ROM or floppy disk and downloaded to the system through central system terminal 303.

Physicians may access system databases 306 and 308, preferably, through server 302. Database 308 may be accessed for reviewing information such as population statistics. This information could be reviewed, for example, to determine the incidence of specific diseases, responses to treatment, natural history of diseases in a population or across populations. In these instances of use, databases are accessible, but none of the data can be associated with an identifiable patient.

History Information

A significant time savings is achieved by physicians by transferring history generation and maintenance from a physician function to the computer-based system using the system in FIG. 3. This will permit information to be input via system terminals 312, 314, and 316, and via central system terminal 303. As stated, this information may be input by the patient, the physician, or other appropriate entity. This method of information (or data) input is capable of saving as much as 50% of the time involved in an initial direct contact between physician and patient. The reduced time of the direct physician-patient interaction does not degrade the value of the physician-patient interaction as would be the case when a shorter history is taken, which results from demands to see more patients in a fixed time period.

The present invention also results in a more complete history being taken. This is the case even if the physician had unlimited time to spend with each patient. The construction of the medical history employs several techniques to enhance the quality and completeness of medical care. This is accomplished because the facts obtained in the patient history are linked to a number of expert analytic systems that represent the distilled knowledge, clinical expertise, and experience of the best physicians in the world. These experts will maintain the expert systems on a day-to-day basis. Thus, the expert analytic systems are always up-to-date with the state of the medical art in each sub-field of medical practice. The educational information that is provided is in real-time and directed to a specific patient's medical needs. Additionally, computer-acquired histories are stored centrally and the patient or physician may readily have access to the information that is stored, for example, in database 306.

A representative method of the present invention for obtaining and storing medical history information will now be discussed referring to FIG. 3. The system processor 304 through rules database 407A (FIG. 4) and, for example, system terminal 312, first requests the patient's name, date of birth, and gender. The date of birth is used to automatically calculate the patient's age. The patients's age is used as a factor in generating the differential diagnosis that is derived from analysis of the patient's medical history and other medically relevant facts that are entered into the patient's database subsequent to acquisition of the complete medical history. The patient's gender is used by the system to activate questions at an appropriate time in the history construction session.

The system processor 304 through, for example, system terminal 312, also collects relevant information about the patient's medical insurance. This insurance information is used to generate a link between the physician and the patient's health insurer. This link can be used to automatically transmit and receive information from the insurer via, for example, e-mails. This will assist in acquiring the appropriate approvals for specific treatment plans, admission to hospital, and other reasons. This link with the patient's health insurer can be used too to send e-mails containing reports derived by computer-acquired and -analyzed medical data, which may be important for prior approval of treatment plans or hospitalization of a patient.

FIG. 4, at 400, shows a diagram of the operation of central system 301 shown in FIG. 3. These operations will be described in a manner that will show how the system of the present invention controls the processing of information among the patient, physician, external inputs, and system databases.

Database 407A contains the rules for acquiring a complete medical history from any patient independent of the nature of patient's complaints or underlying disease. These rules will not require intervention of medical personnel. Database 407A is software constructed on the basis of the rules of physiology, pathology, pathophysiology, biochemistry, pharmacology, microbiology, and clinical observations that are the basis for the rational practice of medicine, independent of the nature of a patient's medical problem. These rules are constructed from the accumulated experience and knowledge of leading physicians and are updated to reflect new knowledge as it becomes available. The present invention also may employ a universal patient interface ("UPI") to facilitate taking the patient's medical history.

Database 407A sends all factual information to the patient's unique set of medical facts that are stored in database 402. Database 402 is the analog of doctor-acquired patient history 102 (FIG. 1), which was recorded in-part and sought to be remembered in-part by the physician. Gathered information in database 102 is based on subjective decisions by the physician through experience and interviews with the patient. Database 402 stores all the historical information relating to medical events or lack thereof across the whole of the patient's life and the patient's family life. It also stores relevant medical data obtained subsequent to the history being taken,e.g., physical examinations, image data, laboratory data.

In a traditional physician-patient interaction, for example, the first question asked of the patient is to describe why medical assistance is sought. This description is meant to be in the patient's own words and obtained without prompting by the physician. This is called the "chief complaint." The present invention obtains the patient's description of their chief complaint, preferably, in this manner. In the preferred embodiment of the present invention, the patient types in their chief complaint when prompted by a computer screen. Alternatively, the patient, who has no familiarity or access to a computer or to an Internet connection, can respond orally to questions via the telephone to the central system processor 304 (FIG. 3) that contains all the information and logic systems available by a direct computer interface. This is done through the use of a UPI of the present invention.

The UPI preferably is in the form of a system terminal such as 312, 314, or 316 shown in FIG. 3. The UPI provides a novel system for inputting information to, and retrieval of information from the system. The UPI makes it possible to access a differential diagnosis via logical operation on the historical data base, independent of the nature of the patient's complaints. The UPI makes it possible to move the history efficiently from general types of subjective complaints, e.g., "a chief complaint of pain" to specific questions about specific diseases in specific organ systems, which could be the ultimate singular cause of a chief complaint of pain.

Prior art systems that are currently being used do not use a UPI to construction logical histories. The UPI permits the taking of a complete medically and medically sound history for any patient regardless of the nature of the patients complaint. A chief complaint, for example, is a non-specific symptom or set of symptoms, e.g., pain or fever. More precise delineation that specify the location of the pain, e.g., chest pain, abdominal pain are also non-specific.

Machine-acquired history systems that do not have the UPI of the present invention may ask the patient to identify the organ that is the site of disease. However, by contrast, depending on what descriptor applies, the UPI and the system of the present invention permits follow-up questions that use medical knowledge and logic software to fully elaborate the nature of the most acute problems to associate the most pressing complaint with an abnormality in one or another organ system. The present invention also does not introduce bias by suggesting key answers to the patient. The key parts of the history that allow for diagnosis of the organ affected are entered in the patient's own words.

In using UPI 312, questions are formulated by the system according to the established rules of medical practice that are stored in the various components in FIG. 4, as will be described, which includes the entire knowledge base of medical practice information. When questions are not answered in the patient's own words, they are answered yes or no or by selection of one or several possible situations given as a list of possibilities. Feedback loops within and between the systems elements continuously relate specific answers to the entire database in order to make connections between the patient's subjective sensation of disarray and specific pathophysiologic items that could account for the symptoms being reported. Questions are presented to the patient based on the likelihood that they will provide significant information, which is predicated on the analysis of the information collected at each point in the process of history acquisition.

In an alternate to the method for providing a UPI, i.e., for obtaining the chief complaint, the patient is provided with a list, or several lists, of all possible complaints and makes appropriate selections from these lists until the system is satisfied that the patient has described the full nature of the complaint(s) for which they are seeking medical assistance. Analysis of the chief complaint obtained in this manner is the same as the situation of obtaining the chief complaint in the patient's own words.

The history of the chief complaint is obtained as follows. Database 407A asks patient 115 through UPI 312 to input their chief complaint in their own words, as text or spoken words that are converted automatically to text. Database 407B, a component of 407A, searches the patient's input for medically meaningful words and phrases. For example, a common chief complaint (related to the leading cause of death in the United States and other developed societies) contains the phrase ". . . chest pain . . . " or the words "pain" and "chest." These are medically significant words and phrases that are recognized by database 407B. Database 407B searches database 407C for the pathophysiologic entities that are a reasonable set of medical diagnoses and underlying disease processes to account for a chief complaint of "chest pain" or "pain in the chest," e.g., coronary artery disease, esophageal disease, gall bladder disease, trauma to the ribs, lung disease, and possibly other conditions. When the patient enters a chief complaint of pain without an anatomic location, the system automatically asks the patient for the site of pain. Databases 407B and 407C are constructed on the basis of the rules of physiology, pathology, pathophysiology, biochemistry, pharmacology, microbiology, and clinical observations that are the basis for the rational practice of medicine, independent of the nature of a patient's medical problem. These rules are constructed from the accumulated experience and knowledge of the leading physicians and are updated to reflect new knowledge whenever this is necessary.

Next, database 407C, through database 407A and 407B, searches database 402 for the patient's prior answers to questions about age and gender (or whatever other questions have been asked and answered previously). Database 407C contains rules by which the likelihood of the diagnostic entities called up in response to the key words "chest pain" are matched versus the patient's other characteristics. The logic of these rules, in this particular instance of the history, is to use the chief complaint and other information about the patient, e.g., age, gender, to formulate a set of working diagnostic possibilities. The accumulated medical knowledge stored in the databases recognizes what prudent physicians know about chest pain: the combination of chest pain, male gender, and age 50 make coronary artery disease a highly likely diagnosis to explain chest pain. This is also an important diagnosis to exclude in a 50 year old man with chest pain because the patient's life is threatened. By contrast, the diagnosis of heart disease is highly unlikely in a 25-year old woman with chest pain. The prudent physician proceeds in the former case to ask first a set of questions with which the diagnosis of heart disease is reinforced or excluded before considering questions that will do the same for other diagnostic possibilities. In the young woman, however, the first set of questions formulated will inquire about diagnoses other than heart disease because the latter is so unlikely. This logical, clinically based approach of the prudent physician is mimicked by the present invention as it acquires a history. Thus, database 407C determines in the case of a middle aged man that the patient should be questioned first about possible coronary artery disease as a cause of his chest pain, but determines that the young woman should be questioned first about possible esophageal disease, even though both patients entered the same—or even identical description of their chief complaint.

The system determines from the chief complaint, age, gender, etc. of the patient how to proceed logically to obtain a more complete history about the characteristics of the chief complaint. Thus, after the patient's chief complaint is known, the system of the present invention proceeds to take a detailed history of this complaint, which is referred to in medical parlance as the "history of the present illness," according to the determination made by database 407C or to the working diagnosis. Once database 407C has made this determination, it instructs database 407A to ask, for example, about the character of the middle-aged patient's chest pain in the context of coronary disease. Database 407C also instructs database 408 that the working diagnosis on which history taking is to proceed for the moment is coronary artery disease. The history proceeds through the interactive interaction amongst these databases.

The task of database 408 is to determine on a continuing basis the closeness of match between the patient's "story" of their disease and the working diagnosis selected by database 407C. Database 408 comprises, on an organ system basis, the rules of physiology, pathology, pathophysiology, biochemistry, pharmacology, microbiology, and clinical observations that are the basis for the rational practice of medicine, independent of the nature of a patient's medical problem. Database 408 is informed not only by the accumulated knowledge and experience of the leading physicians but also is connected on-line to databases 105 and 106, from which it can extract relevant information on the basis of the details of a patient's medical history and formulations of diagnoses derived therefrom.

History taking proceeds with the characterization of the patient's chief complaint of chest pain in this example as follows:

As stated, the patients input the quality of pain in their own words, by text or orally. Database 407D searches for key words related to quality of the pain to associate the key words about quality with the description in the chief complaint and all other facts acquired from the patient, again in the context of the working diagnosis previously determined. Database 407A then asks questions to determine the duration of pain, whether it is worsening or not and so on.

Database 407A next asks the patient to illustrate the location and radiation of pain. Through UPI 312 the patient is asked to locate the precise areas of pain by displaying appropriate anatomic regions of the body. In the example being discussed, for which "chest" defines the region of pain, the database automatically recognizes the need to display anterior, posterior, and lateral views of the chest that are sex appropriate.

The computer database again exactly simulates the questioning of the ideal physician by asking the patient to point and click with the mouse to illustrate the exact region in which pain is occurring. This technique is used to determine whether the pain is localized, diffuse, and the extent of the region(s) affected. The system of the present invention also uses this technique to ask the patient to illustrate the variation of pain with location. The radiation of pain from the site of origin is determined in this way too.

The system converts the patient's responses of pointing and clicking to appropriate textual descriptions of the location of pain. Databases analyze the anatomic description in the context of the working diagnosis and other possible diagnoses compatible with the historical facts already collected. This can be done on the basis of locations on the anatomic diagrams or after conversion of graphic answers to text. The graphic descriptions (anatomic cartoons overlaid with mouse clicks or sweeps) are saved in database 402. These may be later displayed for examination by the physician on demand or as part of the report sent to the physician.

Graphic displays to the patient are not limited to anatomic cartoons for locating pain. They could comprise of actual photographs, for example, of rashes or other lesions of the surface of the body, eyes, mouth, and so on which the patient would identify as the same as or similar to a lesion on their body.

As in the use of other databases just described for characterizing the patient's chief complaint, the graphic representation of anatomic features of pain are analyzed against rules contained within database 407E, which is instructed as to the working diagnosis by database 408. Database 408 estimates continuously the closeness of match between the patient's subjective description of pain and its physical characteristics and the characteristics of pain associated with the working diagnosis (coronary artery disease in this example) that is driving the formulations of questions.

Depending on matches of answers with what is reasonable for the working diagnosis, this process continues in the context the working diagnosis of coronary artery disease until the program determines that the pain does or does not have the properties of coronary artery disease. This may be achieved by matching the patient's database of pain versus case studies or by using any number of different statistical programs to evaluate the totality of the complaint.

As is often the case at this stage of the patient's interactions with the health care system, the databases may not determine that one or another diagnosis can be made or excluded with certainty. In this case, all possible diagnostic leads are pursued according to the operation of the various databases just outlined. All reasonable working diagnoses are included in the final differential diagnosis together with appropriate guidelines for objective testing to reach as definitive diagnosis. Thus, on a continuing basis, database 408 evaluates the data to form the list of differential diagnoses that are output to database 404.

Once "the history of the present illness is completed," the other features of a complete medical history are obtained. In this phase of the history-taking, as in the "chief complaint" and "history of present illness," the system poses leading questions to cover all possible risk factors for disease and evidence of clinically manifest disease in the patient's organ systems. This process leads to the building of a series of questions to follow-up the responses to the leading positive and negative questions. For example, a leading question may be: "Do you or have you ever smoked?" Follow-up questions to a positive answer would determine the length of smoking, the amount of smoking, and questions seeking detailed evidence for the presence or absence of dysfunction in organ systems, e.g. the heart and lung, that are damaged by smoking.

In this way, the system acquires all other elements of a complete medical history: social and family history, history of past hospitalization to name a few. In the case of the family history, the system collates the data to prepare a graphic of the family pedigree and analyzes the data to determine the genetic basis for the disease, autosomal-sex linked recessive or dominant. The system also determines whether a family history of disease indicates a Mendeliam inheritance or random occurrence.

The system automatically prepares letters to acquire prior medical records in response to inputs of sites of prior hospitalization and prior physicians. At a time when patient files are no longer stored as handwritten records, the system finds and analyzes the content in prior electronically stored medical records.

An especially important and timesaving feature of the history-taking component of the present invention is the manner in which the patient is questioned about the use of medications. The patient is asked to type in the names of all medications (prescription and non-prescription) he/she is taking along with exact dosage by typing into their history file the exact wording of the labels on each. This inquiry also asks for the number of pills prescribed, the number remaining, and the date of the prescription. From this, the system calculates whether or not the patient has been compliant in taking any or all of their medications. The list of drugs and dosage typed in by the patient triggers a search of the data entered by a database that scans the entries of drugs for potential incompatibility of drugs and possible adverse drug-drug interactions for a given patient. Moreover, when new medications are prescribed, the system of the present invention scans the patient's list of drugs to search for incompatibilities between drugs, and contra-indications to specific combinations of drugs. The system warns the physician whenever a dangerous condition exists with regard to the medications that are prescribed.

The drug information in the databases of the present invention rationalizes the medications being taken with all other data in the medical history to determine the conditions for which each medication is indicated and to determine whether medications have been prescribed appropriately.

The collection of a complete history of all medications being used by the patient is a basis for being certain that the patient's physician is knowledgeable about potential adverse effects of the medications the patient is taking as well knowledgeable about any potentially adverse effects because of the combination of drugs the patient may be taking. This information is sent automatically to the physician on the basis of the data acquired by the history component of the present invention because the system searches a separate database comprising knowledge on the pharmacology and toxic potential for all agents taken by a given patient. On this basis too, the physician is given explicit information on the most efficient manner in which to monitor the patient for the early onset of the possible adverse effects for which there is risk in a given patient. The physician is also informed of the conditions under which any drug should be stopped or substituted for because of either a sub-clinical or clinically overt adverse reaction. This knowledge and the documentation for it, in the form of relevant literature, is provided as part of the reports sent automatically to the doctor whenever the system detects that change has occurred in the patient's medical status. This reporting will be explained in describing FIG. 5.

When history taking and analysis of acquired historical data are completed by the system of the present invention, the system proceeds by searching database 409 for guidelines illustrating the most efficient methods for confirming/excluding the diagnostic entities in the differential diagnosis. This search includes finding methods for evaluating the extent of harm due to risk factors for disease identified by the history taking process. The system also proceeds with a search of therapeutic database 410 to define the most efficient and safe method(s) for treating each specific medical problem and/or risk factor in each specific patient. The historical database acquired from the patient interacts iteratively and automatically with diagnostic and therapeutic databases to insure that the recommended treatments are appropriate for the uniqueness of the medical setting that can exist in individual patients.

A further task undertaken automatically according to the present invention, is that once history taking and analysis of acquired historical data are completed, it will use the outputs of database 404 and 408 as the search tools for searching the body of medical knowledge in books, medical journals, or any other archives of stored medical knowledge, for the most up-to-date medical knowledge relating to the diagnosis and treatment of each medical problem or risk factor for disease that has been identified by the software databases of the current invention. This search includes searching databases 105 and 106.

A still further task undertaken by the system and method of the present invention at the completion of the above tasks, is to use the analytic results, i.e., the specific identification of medical problems and risk factors in a given patient, that might be unique to a given patient, to search databases of medical knowledge that are appropriate for patient education.

FIG. 5, generally at 500, shows the reporting structure for the present invention. When all analyses and database searches are completed, all relevant material is compiled in report form, arranged according to category: facts of medical history, interpretation of facts in the context of differential diagnoses for each medical problem identified, guidelines and pathway for correct and efficient method(s) for making exact diagnoses for each medical problem and/or risk factor identified, guidelines for treatment, and recommendations for treatment. The report includes both citations and text of relevant literature to each medical problem identified in each patient and to the most efficient processes for diagnosing each condition and then for treating each of those for which a diagnosis ultimately will be made. Accordingly, the report will have different components for the various databases. For example, the report may include section 502 from database 105, section 504 from database 106, section 506 from database 410, section 508 from database 404, and section 510 from database 409. It is understood that the report may include information for more or less than these databases or other information and still be within the scope of the present invention.

In the preferred embodiment of the invention, the report is sent to the patient's doctor by e-mail so that the details of the patient's medical history, risk factors, possible diagnoses for current and past problems, past medical history, and familiar risks are known to the doctor prior to a first encounter with the patient. The report could be sent, however, as a voice mail, which the doctor could review on a tape. The report also could be sent as a hard copy text.

A separate e-mail report identifying the likely medical problems and risk factors in a given patient is sent to the patient at the end of the patient's session. This report includes appropriate educational material tied automatically to specific analysis of the specific details of each patient's complete medical history.

The present invention, therefore, is a computer-based system and method which constructs medical histories by direct interactions between the patient and the system that acquires pertinent and relevant medical information covering the complete life of a given patient. The present invention insures that a complete life long medical history is acquired from every patient interacting with the health care system. Once acquired, the facts of the patient's life long and family medical history are analyzed automatically by databases to generate a set of the most reasonable diagnostic possibilities (the differential diagnosis) for each medical problem identified and for each risk factor for disease that is uncovered in the historical database. Further, the automatically analyzed database of historical medical information is used as the search tool for bringing to bear, on the diagnosis and treatment of each medical problem identified in each patient, the entirety of medical knowledge that relates to and can be useful for the correct and efficient diagnosis and treatment of each of every patient's medical problems.

The present invention insures a high and uniform level of quality in medical care for all patients independent of the medical knowledge and clinical experience acquired and stored by a patient's doctor prior to the first patient-doctor interaction. The interaction between patient and the present invention occurs prior to interaction between the doctor and the patient and occurs independently of direct inputs from the doctor, except for giving the patient a computer code that links the patient's history to computer terminals, PDAs, and so on to which the patient's chosen doctor and/or members of the doctor's staff have secure access.

The present invention removes variability in the quality of medical care that currently exists because of the variable store of specific medical knowledge and clinical experience (data 101 in each physician's mind) and/or the ability to recall specific relevant parts of data in response to specific problems in specific patients and the reliance on variable clinical experience, from doctor to doctor, that typically informs the practice of individual doctors.

The present invention makes obsolete the faulty paradigm of using the variable medical knowledge and clinical expertise of single physicians for acquiring a medical history. The system and method of the present invention are tools by which the accumulated medical expertise and clinical experience of the best physicians becomes the basis for clinical care for every patient needing medical. This accumulated knowledge and experience are interposed between patient and doctor, in the form of software programs that collect the medical database represented by a patient's medical history and that interpret this database.

The system and method of the present invention minimize the differences in outcomes from health care because the variable past knowledge and/or training of a physician or to variable abilities of physicians to recall specific bodies of knowledge that are or will be immediately relevant for the efficient and correct diagnosis and treatment of a patient. The present invention obviates the possibility that a physician will not be aware of deficiencies in his/her current state of medical knowledge that applies to a specific problem or problem(s) in a given patient. This is because the present invention uses the detailed medical needs of each patient as a basis for automatically identifying, assembling, and bringing to the physician's immediate attention in the clinical setting, the body of medical knowledge that represents the most current sets of medical facts and rules for diagnosis and management of which a physician should be aware in order to be thorough, correct, and efficient in the process of diagnosis and management of each specific medical problem and/or risk factor identified in each specific patient in a practice, independently of the nature of a medical problem.

The system and method of the present invention remove the possibility that a patient's medical problem, independent of its nature, can be diagnosed and treated in a context removed from state of the art medical knowledge applying to the diagnosis and treatment of that specific condition. This is achieved because it automatically collects and determines what are the detailed medical needs of each patient interacting with the invention and then it uses this information to identify, assemble, and deliver to the doctor's immediate attention in the clinical setting. This will be the medical knowledge, from that extent, that represents the most current sets of medical facts and rules for diagnosis and management of which a doctor should be aware to be thorough, correct and efficient in the process of diagnosis and management of each medical problem and/or risk factor identified in each patient.

The following is representative history-taking according to the present invention:

1. New Patient, First Significant Contact with the Health Care System.

The physician's secretary or other assistant determines whether the patient has been a previous system subscriber. If not, and the patient has an Internet connection at home, the patient is given a login code for access to the system of the present invention. At this time or later, the patient and doctor are provided a security card or other means to access to the patient information. Once the patient has logged on, a file can be created and the medical history elicited prior to the patient's visit to the physician's office (or clinic). Alternatively, the patient may be instructed to use a suitable computer terminal in a public place, like a library or bank, or to access the system by phone.

The system of the present invention may be deployed in non-public areas, such as an emergency room setting. In such a setting, the system and method of the invention may be used for triage of patients. Deployed in the private, non-public, or triage settings of the system and method of the present invention, can save patients considerable time. This is particularly true if the patient is in an emergency room. The present invention can reduce the crowding of emergency rooms by handling patients more efficiently which ultimately leads better use of hospital emergency room facilities.

The likelihood that a true emergency problem exists in a given patient or whether the patient can be taken care of in a less acute setting may be readily determined through use of the system and method of the present invention. Additionally, the system can make immediate determinations as to whether and what types of laboratory testing is appropriate (or not) in the emergency room setting whether acute or chronic. As such, there is an opportunity to order appropriate laboratory tests and have them completed prior to the time a patient with or without an emergency is seen by a physician. This saves time for the patient, while enhancing their sense that they are being cared for. The decrease in crowding in emergency rooms by decreasing the time needed to make a disposition in a given patient is highly desirable. Thus, in the emergency room setting, the history-taking feature may be applied to gather the medically necessary information and have it placed into the system of the present invention to prepare the physician prior to seeing the patient.

At the end of a history-taking session for a patient new to the system, the present invention prepares a report for the physician and a report for the patient, each of which is based on an analysis of the historical data obtained from the patient. These reports will be in accordance with FIG. 5.

2. The Report to the Physician.

The report to the physician is sent by e-mail from central processor 304 to the physician's system terminal, such as system terminal 314. System processor 304 performs the analytic evaluations of the history data. System terminal 314 may be in the physician's office or the physician's home. The e-mails will be displayed on the display screen of physician's system terminal 314 or may be printed out. In a busy emergency room setting, the physician's PDA may be alerted that a report has been sent or the physician's pager can be alerted. Alternatively, the report may be sent via facsimile. In the emergency room setting, the report can be printed out directly for the physician to see or displayed on a computer terminal in the emergency room or at a remote site or sent simultaneously to different physicians at separate sites. By whatever means of communication, the purpose of the report to the physician is to provide the necessary information to the physician before he/she sees the patient. This accomplishes at least two things: first, there is a large time savings and, second, preservation of the physician-patient relationship. A third purpose of the report is to insure that the physician has continuing education material from database 408 that allows him/her to incorporate the current state of relevant medical art in the treatment of each of a given patient's specific medical problems.

The report to the physician has the following preferred components:
  (i) a verbatim record of the patient's chief complaint together with important modifiers of the chief complaint,
  (ii) a list of the diagnostic entities reviewed in detail by the system, on the basis of the patient's chief complaint,
  (iii) a list of the working differential diagnosis, which is the list of items considered as possible causes of the chief complaint on the basis of the complete medical history,
  (iv) a comparison of the initial and working differential diagnoses which indicates to the physician what pathophysiologic items are being considered at the beginning of the history-taking session and are excluded by the complete history,
  (v) a list of all other medical issues and risk factors for disease identified by the computer analysis,
  (vi) a list of all medications being taken by the patient, and
  (vii) a list of all risks engendered by the ingestion of these medications.

Besides these general characteristics, the report to the physician contains the following types of information.
  A. The items in the differential diagnosis listed by priority of diagnosis for each medical problem identified from the historical database, i.e., the chief complaint plus any other problems the patient may have revealed during interrogation by the present invention. This list is generated from the combined database history-information and comparison of the patient's disease profile with the database for all patients with similar disease profiles for whom the outcome—true diagnoses and responses to different specific types of treatment are known. This information on outcomes is in the databases for patients who are evaluated and followed by the components of the system of the present invention. The outcomes data are refined continuously by analysis of the databases for all other patients enrolled by the system, as their outcomes become known.
  B. The system annotates the items in the working differential diagnosis with guidelines for objective testing that is useful for confirming or excluding each of the items in the differential diagnosis. These guidelines indicate how to determine the severity of disease, and to institute therapy after confirmation of the diagnosis. All guidelines are formulated to reach a diagnosis in the most efficient way in terms of time and cost.
  C. Specific risk factors are identified that can impact the patient's health, for example, as the history of high intake of alcohol, allergies to certain drugs, and so on. These risk factors may or may not require monitoring or diagnostic evaluation.
  D. The analysis of the patient's database by system processor 304 results in the output of a list of key physical findings that should be investigated or excluded because the presence or absence of the specific findings is important for further refinement of the working diagnosis, leading to a final, definitive diagnosis.
  E. The first report estimates the urgency with which the physician should see the patient.
  F. The first report identifies laboratory tests that will refine the working diagnoses to obtain a final definitive diagnosis, independent of results from the physical examination. The report provides a link for the physician to order the laboratory tests selected by the system analysis of the historical database. The physician can accept, modify, or reject any entry in the order form. The physician can send the order form to the patient via e-mail with instructions on how to prepare for tests and the most convenient sites at which the tests can be carried out. This feature of the present invention enables the physician to have important laboratory data relevant to the items in the differential diagnosis prior to the first visit with the patient. In the case that the patient does not have e-mail, the orders for laboratory testing can be sent directly to a suitable testing site and the patient informed by telephone, by facsimile, or by other means, and the person to contact in order to complete the indicated tests. The system automatically transmits authorization for all laboratory testing by e-mail message to the appropriate laboratory.
  G. The first report has up-to-date reviews of the medical literature that are relevant to the items in the working diagnosis and to any other risk factors identified by the analysis of the patient's history. The physician may read this material from a computer display screen or it can be printed out in a hard copy, including text, medically significant images, graphic displays of data, and references for further reading. In addition to the reviews, the physician may follow prompts to further relevant literature for any depth of understanding.

H. The system detects when a field that is relevant to the patient's medical care is empty. The system reminds the physician of this on a continuing basis. This reminder is that an important field is empty, what this field is, the medical information needed for filling it, and why the information is important. The empty field may or may not be relevant to the patient's working diagnoses or final diagnosis. The empty field problem may be solved at each follow-up visit, or as reminders to call the patient back to complete relevant medical needs, on a weekly basis, or monthly basis.

The summary analysis of each patient's database, viz., the differential diagnosis and the alerts to conditions not related directly to the differential, is only one of the ways in which the physician may review the historical database. The physician may examine the complete database of each patient in order to verify specific answers to any question in any section of the history. The complete, detailed history can be retrieved at a system terminal for the purpose of studying specific answers and constellations of answers only if the physician has been given access to the patient information by the patient via System Control and Storage 750 (FIG. 7). Input of specific answers brings up the complete file of questions and answers related to a specific area of questioning. The decision tree by which the system determines the sequence of questions (with the patient-specified answers) is displayed. The physician may review sections of the detailed history, by clicking the appropriate link, for example, for all materials related to the heart, or gastrointestinal system, or any other organ.

The continuing education aspect of the present invention allows the physician to follow the logic by which items in the differential diagnosis are derived from the chief complaint and determine what was excluded by facts in the subsequent history. Given this, the physician may determine the logic by which items in the working diagnosis were determined. Activation of the diagnostic item activates each of these learning tools.

Noting the foregoing, the physician may review a patient's history and this review will have two critical effects on the manner in which the physician practices medicine. First, the physician will be completely familiar with the patient's medical history prior to the time of the first face-to-face meeting. This saves valuable physician time while also insuring that a truly complete and up-to-date medical history has been obtained for all patients in the physician's practice. Second, the physician, prior to seeing the patient, has had the time to familiarize himself/herself with the state of medical knowledge for any and all the medical issues that are or will be presented by each patient in his/her practice. This, in turn, (i) keeps the physician up-to-date with the latest developments in clinical knowledge that affect specific patients for whom educational material is provided; (ii) extends the range of diseases that any single physician can diagnose (and treat) effectively; and (iii) enhances the quality of care a patient is likely to receive from any physician.

3. Computer Generated Report for the Patient

In addition to reporting results to the physician of medical analysis of the patient's history, an analysis of the patient's history is sent to the patient. The purpose of this report is to identify to the patient the medical risk factors, whether related or not to the working diagnosis, over which the patient has control. The report provides an analysis of the patient's individual risks and educational material for helping the patient modify (or mitigate) this risk. As in the reports to the physician, the educational material provided to the patient is individualized on the basis of the patient's specific risks, age, other medical conditions, and family history.

The system of the present invention also retains information that it obtained in the past about each patient and follows-up on these discoveries to reinforce the patient's resolve to alter risky behavior. Reminders are also provided to the patient to determine whether or not the patient has been compliant with making needed life style changes to reduce the risk and morbidity of disease. This happens whenever the patient logs on to his/her file as part of the follow-up and treatment. The patient's response to educational material about the risk factors in their lives also can be reinforced by periodic e-mails sent automatically. Educational material that is sent is intended to be directly applicable to a patient's specific problems and written at a level for lay people to understand. This material is culled automatically from printed material or from websites on the Internet.

4. Inputs Added After Completion of the History

The physician may add inputs to the patient's medical file (for which the history is only the first component) e.g., from a physical examination. The physical findings may be added orally as the physician examines the patient. In this case, the oral message is translated to text that is searched for key words by the database appropriate for each type of physical finding. The search for key words links the textual content to all other facts in the patient's medical file. This permits a consistent and seamless interpretation of any and all physical finding in the context of all of the other data in the file. Alternatively, the physician or an assistant may enter the physical findings as text. These entries will be searched for meaning by appropriate databases, or by response to a predetermined list of check-off forms that appear on the computer screen. Graphics of different regions of the body can be called up for precise locations of anatomic findings.

Laboratory data also may be entered into the patient's database. In the preferred embodiment of the invention, the laboratory performing the tests has a direct connection to system server 302 and system processor 304 through control system terminal 313. This on-line connection will efficiently provide the information to the physician who may be using system terminal 314. Laboratory data that represent images, such as X-rays, MRI scans, CAT scan, and other appropriate modalities, or that are interpretations derived from biopsy of tissues or collections of cells from tissue (cytology) are added as images to the patient's file, along with interpretations of the images. Textual reports can be entered on-line as text, or entered orally and converted to text. Textual laboratory results are searched for medical meaning by a database appropriate for the type of examination. The database appropriate for searching a specific type of textual report, e.g., for a chest X-ray, for an MRI of the head, or for a CAT scan is identified automatically by an entry code or by key words in the text. For example, the interpretation of a liver biopsy may indicate that the pathologist examined a sample of liver. The word "liver" would trigger a search of the interpretation of the textual report by the database for liver biopsies.

The present invention uses rules to control the content of subjective interpretations of laboratory data, i.e., interpretations that are textual and not numerical. An appropriate rule is that the content of a subjective report must conform to the standard for interpreting X-rays, other images modalities, and biopsies. For example, liver biopsies are done to evaluate the risk/benefit for treatment of hepatitis C. The risk/benefit interpretation of the liver biopsy depends on reporting the degree of disease activity (a numerical value indicated for degree of activity) and the stage of liver disease (a numerical value indicated for stage) as reflected by fibrosis. Many pathologists do not interpret liver biopsies in this way.

The system and method of the present invention will not accept the text for a liver biopsy, in a patient with hepatitis C unless numerical data are given for activity and stage. As specified by conscientious panels of authorities, the report for the liver biopsy incorporated into the patient's database will indicate that the interpretation is inadequate. Additionally, the system and method of the present invention will send an e-mail to the reporting department that the report is inadequate, that it is below the standard of care, and that the biopsy must be reinterpreted according to established guidelines, which will be appended to the e-mail. Reminders are sent by e-mail until the sending department corrects the deficiency.

5. Incorporation of New Entries into the Complete Database of Each Patient

Each time a new entry is added to a patient's file by a physician, patient, physician's assistant, or reporting laboratory, the patient's complete file is reanalyzed in light of the newly added data. The physician is notified by e-mail of the new laboratory results. If entries, e.g., physical findings, laboratory data, alter the differential diagnosis, either confirming, adding, or removing possible diagnoses, the results of the analysis signaling such a change in the status of the patient's evaluation are again e-mailed to the physician's system terminal 314. This will be presented along with any additional educational information that is relevant to a change in the diagnostic possibilities.

6. Computer Generated Guidelines for the Management of Patients

The system and method of the present invention guides the physician continuously in moving the diagnostic process from the working diagnosis to a final, definitive diagnosis. This is achieved by indicating what laboratory data are needed, interpreting laboratory data as it is entered into the patient's file, and continuously updating the decision support systems and the textual educational materials that are relevant to the patient's problem and progress. All guidelines based on automated analysis of a patient's file may be communicated by e-mail.

Once a final, definitive diagnosis is made, the system provides regimens for treatment that are based on each patient's unique medical database. The recommendations for treatment are based on the diagnosis, evidence for severity of disease, risk factors applicable to the patient, such as drugs taken for other conditions, age, and analysis of outcomes for all patients corresponding to the disease profile of the patient of interest. The system provides risk/benefit analyses for different possible therapies or treatments that are based again on specific details of a specific patient's medical condition.

System processor 304 and system processor 306 (which may includes the databases 402, 404, 407(A-I), 408, 409, and 410 (FIGS. 4 and 5) or other method databases) provides the physician with guidelines for the selection of specific medications for treating specific problems in individual patients. The system generates a list of drugs and their doses that are acceptable and a list of those drugs for which there are relative and absolute contra-indications. Computer-based decisions in this regard automatically exclude drugs that will interact adversely with other medications the patient is taking or that are contra-indicated by some factor in the patient's medical history. The system and method create links to reviews and primary medical literature so that the physician may obtain the documentation for the therapeutic recommendations, including those drugs for which there are contra-indications to use.

All prescriptions are written into the database for each patient. The system is able to prevent the physician from making inadvertent errors in prescribing. Should a physician ignore the preferred list of antibiotics that are given and prescribe, for example, penicillin (or an antibiotic with cross-reaction to penicillin), the system examines the patient's medical database to determine whether there is a history of an allergic reaction to penicillin or related antibiotics. If so, the system and method of the present invention will prevent the recommendation of a prescription for penicillin and sends the physician an alert as to why the specific prescription cannot be filled. Another example of the utility of this feature is a failure to transmit a prescription for penicillin in the event that a history contains no information on an allergic reaction to penicillin in the database and that this fact needs to be established.

In this specific setting, the physician may enter the prescription into the patient's database by typing in the prescription, by oral command that is translated to text, or the prescription can be entered by a physician's aide. The textual entry is checked by an appropriate database that logically links the word penicillin, when it is entered, to a search for evidence or lack thereof for an allergic reaction to penicillin or related antibiotics. This search occurs in real-time, and the results of the search are provided to the physician on the computer display screen: either the prescription is approved or disapproved for the reasons shown on the screen.

Another example of logic based checking of the appropriate database to determine the suitability of a given prescription is a search for contraindications to administration of a given drug. The anti-seizure drug valproic acid, for example, can be toxic to the liver. It is contra-indicated in patients with a history of liver disease or evidence of liver disease. In the event that a prescription for valproic acid is written inadvertently for a patient with a database entry positive for a history of liver disease or for a patient with abnormal chemical tests of liver function, the system and method of the present invention send a message to block administration of this drug, while providing alternate possibilities for treatment.

Once an acceptable prescription has been entered into the database for a specific patient, the system and method generate a new set of guidelines for monitoring the patient's progress during treatment. As with all other guidelines, the ones for treatment are based on automated analyses of the patient's medical file in the context of specifics that apply to the patient and the treatment chosen. Specific features provided in this way are a timetable for measuring progress based on achievable goals for patients with the same diagnosis as the patient of interest.

The system and method of the present invention also provide a list of the ways in which progress can be monitored by following clinical signs of disease, symptoms of disease, and laboratory evidence of disease. The timetable indicates the time over which each index of disease should improve, how much it should improve, and what is an acceptable result from treatment in the context of these measures of disease. The guidelines also include a list of the side effects that may occur from treatment. This information is based on the drug being selected, the complete medical history of the patient, and what other medications the patient may be taking. The physician and the patient are alerted by the system to symptomatic changes indicative of an adverse reaction to the treatment regime, clinical signs of the same, and laboratory evidence of the same.

A timetable for searching for laboratory evidence of adverse reactions to medications is given as well. This information is provided automatically in different versions to the physician and patient. Links provide access to the medical literature documenting the adverse reactions to a given agent, how to detect adverse reactions, and how to manage them. These links also provide educational material for determining how therapy can be modified in the case of an adverse reaction to the first drug of choice.

Guidelines for treatment and guidelines for monitoring the patient's response to treatment are not limited to lists of drugs or tracking of responses to drugs. Guidelines of both types are provided automatically when needed. This is true even in the absence of the need to treat with medications.

7. Follow-Up of Old Patient Already Enrolled in the System of the Current Invention.

According to the present invention, patients are tracked as indicated above, until they leave the system, e.g., during the time it takes to make a definitive diagnosis and during the course of therapy, whether for an acute or chronic illness. The system, however, may change the standard means by which the patient and physician stay in contact, and the manner in which follow-up visits are scheduled.

By using the system and method of the present invention, a patient stays in constant contact with his/her physician to report changes in their medical state and to request information, and to be reassured by reference to their centrally located complete medical history database and analytic systems of the present invention. That is, the patient can interact to add information to their databases as appropriate whenever they believe contact is needed. The physician stays in constant contact with each patient in the same way—via the centrally located medical history database. The patient's medical history database also stays in constant contact with the physician independent of the patient's perception of changes in their medical status. For example, the physician is notified whenever a significant medical fact is added by a laboratory to the patient's medical history database, and whenever the patient adds a significant fact to their medical history database. The physician also is alerted to a material change in a patient's medical history database whenever an advance in medical science applies to a patient in their practice.

Central system databases 306 and 308, plus the searching utility of system processor 304, insures the rapid dissemination of new knowledge to the physicians caring for patients. In the preferred embodiment of the present invention, expert panels of physicians constantly refine the bodies of knowledge and logic systems of the fields of medicine for which they are responsible. When these panels deem that an advance in medical knowledge is beneficial for diagnosis and/or treatment of a disease, this new information is incorporated into the analytic systems of the present invention. When new information is incorporated in this manner, it is tagged so that all files may be searched to determine which patient's already enrolled in the system can benefit from the new knowledge. E-mail messages are sent to treating physicians alerting them to the new knowledge, identifying for the physician only the patients in the practice who will benefit from application of the new knowledge, and providing the educational materials that document the use of the new knowledge. In cases when the new knowledge applies to treatment, it is incorporated into the analytic systems along with appropriate guidelines on use of the treatment, the time frame for expected responses, the possible hazards of treatment with a new agent or device, and how to monitor them. Additionally, if treatment is commenced with a newly introduced agent, the system can establish links to the FDA and/or to the manufacturer of a device or drug for on-line reporting of adverse events should they occur.

8. Specifics for Incorporation of Follow-Up Data into the Database for Each Patient The patient adds to his/her medical history database by the method used to initiate the database at regularly scheduled intervals, e.g., every day or every week, as determined by the physician in order to establish a record of the patient's progress or lack thereof, or when the need arises. The system and method of the present invention are configured to interrogate the patient in two related contexts: (1) the diagnosis for the patient's chief complaint and any other problems for which observation is important or for which therapy has been undertaken and (2) the expectation of good or poor responses to the therapy that is deemed appropriate for the problems from which the patient suffers. For example, queries are posited on the basis of the already acquired database for a specific diagnosis and the method being used to treat the underlying disease. With regard to the primary database that was acquired, questions are based on knowledge-based systems constructed with specific types of reasoning. Besides acquiring information about the patient's subjective and possibly objective responses to medications, the system may query the patient about the following issues:

A. Changes in the symptoms of which the patient complained initially.

B. Changes in physical evidence for the patient's disease, which the patient has been instructed to observe and that can be observed directly.

C. Appearance of new symptoms. The system, as described for the chief complaint above, analyzes any new complaints. When a new complaint(s) is recognized, the appropriate subsystem(s) reacquires the important facts pertaining to possible disease not previously identified.

D. Appearance of new physical evidence of disease. When new physical evidence of disease is entered into the database, the appropriate expert subsystem(s) reacquires the important facts pertaining to possible disease not previously identified.

E. Compliance in administration of prescribed medications.

F. Evidence from the patient of adverse reactions to any medication prescribed. The system interrogates the patient with questions that are based on the known adverse consequences of all the agents a given patient may be taking, the known drug-drug interactions between agents a specific patient may be taking, and any features of the patient that enhance the risk of an adverse reaction.

G. Monitoring of the database for completion of laboratory testing.

H. Queries about organ systems other than the system for which there is initial evidence of disease not related to the chief complaint and to evidence of disease that could reflect progressive deleterious effects secondary to the primary disease state.

E-mail messages are used to alert the physician immediately to changes in status to further enhance the efficiency of the medical care system and diminish health care costs. These are accomplished by giving the physician an opportunity to rethink the clinical problem, acquire additional information from the computer-generated educational materials, collect any important clinical and laboratory information that may indicate a need for a change in treatment or additional testing prior to an office visit by the patient. These also enhance the value of medical care by doing away with arbitrary rescheduling of follow-up visits. The system and method of the present invention make it possible for physicians to follow his/her patients on an immediate, day-to-day basis to determine in detail the progress of each patient. The system and its deployment affords the patient the opportunity to inform his/her physician immediately of any significant change in their medical status.

The system and method of the present invention allows physician-patient and patient-physician meaningful communications in the absence of face-to-face contact. Since these communications always occur through the logic systems of the present invention, data from patients is interpreted prior to communications to the treating physician. That is, all information from the patient to the physician is filtered and interpreted as to its significance by the system. Thus, the system does not allow free communications from patient to physician of information that is not relevant to a patient's medical problem(s) or that is not significant for the patient. This avoids the burden to the physician of collecting or reviewing information that does not add to the value of the physician-patient interaction.

The follow-up components of the present invention, together with the method of their deployment, make it possible to schedule follow-up visits at the precise times they are needed and to avoid follow up visits that will have no value for the patient. Visits that are not medically significant because the patient requires no change in treatment or because no new symptoms or signs of disease have occurred are not scheduled and do not occur. The present invention provides a system and method through which only those follow-up visits occur that will add value to the patient's medical treatment. As such, a follow-up visit can be scheduled immediately when a change in status occurs, as an adverse reaction develops, or when it is apparent that the first prescribed treatment is having less than the desired therapeutic effect. No follow-up visit is scheduled and costly use of physician time, and patient time and expense, occurs when such visits will not be useful for the patient. The present invention, therefore, increases the value of the physician's office time by allowing this time to be used for solving medical problems and avoiding routine visits for which no problem exists.

The system and method of the present invention track the compliance of each patient with scheduled laboratory testing, follow-up entries, and with any other instructions given by the physician as part of the treatment plan. That is, the system reports an alert to the physician in the event that laboratory test results do not appear in the database at the proper time. For example, patients taking anticoagulant drugs in order to prevent formation of blood clots require monitoring of the clotting capacity of their blood. The monitoring insures that neither too small a dose for a therapeutic effect has been given, or that too large a dose, causing a tendency to bleeding, has occurred. Monitoring of the so-called prothrombin time for the above purpose may be at monthly intervals. The physician would be sent an alert should a patient taking anticoagulants fail to have a prothrombin time measured at the right interval of treatment.

The system and method of the present invention can simultaneously alert the patient to the fact that an important event in the treatment regime has been missed. The system sends the patient educational materials that are reminders to the patient of the importance of compliance with laboratory testing and the consequences to the patient's well being of non-compliance.

9. New Patient to a Practice, Who was Previously Enrolled in the System of the Current Invention For the patient with an already established medical file within the system of the present invention, the physician's secretary arranges for a secure access to the existing file by the patient's new physician using System Control and Storage card 750 (FIG. 7) or other appropriate means which may not be a card. The system automatically informs the new physician of all medical issues uncovered over time in the new patient as well as a compilation of all risk factors relevant to the patient's medical state. A history of prior treatment and responses to treatment also are provided. The physician's secretary instructs the patient during the first contact between them to logon to their complete medical file to provide an update on their current medical status. The system of the present invention conducts, in this instance, a follow-up interview of the patient. The system sends the new physician all past important medical information. Any significant new information is sent as an e-mail report to the patient's new physician.

Database Applications of the Invention

The system and method of the present invention provide a mechanism for storing the work product of the health care system, which are the medical histories of patients' diseases, which include the medical history of a patient and all other medically relevant information whether related to diagnosis or treatment, from the onset of disease until resolution or death. The present invention insures that all medical records are complete, that they are stored in an accessible, searchable, analyzable, and legible form. It provides a mechanism for searching for significant medical information by words, by associations of words using any logical search method, or by any other conceivable method using words, phrases, combinations of words and numerical inputs. Additionally, it provides a direct on-line method for using statistical programs of any sort for searching medical files in a database. Important gains of productivity of the health care system are enabled by the present invention because of the manner in which it keeps medical records.

1. The Current Invention Provides a New Method for Conduct of Clinical Research

It is considered, for example, that coronary artery disease is a singular entity, i.e., all patients with coronary artery disease have the identical disease. Thus, outcomes from treatment of this disease normally are lumped together. However, in reality, the disease profiles of patients with coronary artery disease vary widely. Some patient's with coronary artery disease are diabetic, some smoke, some have high levels of cholesterol in their blood, some high blood pressure, while others do not. Some patients with coronary artery disease have one, two, or three or all of the above "risk" factors for coronary artery disease, while some lack all of these risk factors. The age of incidence of coronary artery disease varies widely among patients, who may have none, one, two or more, or all of the risk factors for the disease. And then some patients with coronary artery disease are men and some women.

The present invention makes it possible to study in clinical detail all the patients with coronary artery disease with disease profiles generated from all the different permutations of the risk factors enumerated, e.g., gender, and age, at the onset. This is so because it provides a basis for searching the detailed medical histories of millions of subscribers, who have the diagnosis coronary artery disease. Detailed medical data, more complete than in any clinical protocol ever undertaken to date, will be available by use of the present invention. This is also done at no extra cost to the health care system.

Referring again to the illustration from the New York Times reported on Aug. 4, 1999, the scope of the issue of clinical research available through use of the present invention may be shown. This article reported that Ritalin, studied in 75 boys, did not lead to higher subsequent rates of drug abuse, as was believed previously to be so. The *Times* article noted, however, that approximately 1.5 million boys were taking Ritalin in the United States. No comment was made about the discrepancy between 1.5 million patients taking Ritalin and the availability of detailed information for only 75 patients. But the obvious cause of the discrepancy is the manner in which medical records are acquired and maintained. It's impossible to find the relevant data on the 1,499,925 patients not included in the Ritalin study. Moreover, it is probably impossible to read the charts of these patients if they could be found. There is, as a result, no archive of data on disease except for records of the small minority of patients who have participated in a controlled clinical trial of some sort. This serious deficiency in the health care system is solved by the present invention. The present invention will permit all of the information to be available so that meaningful information may be generated.

The system and method of the present invention may be used to correlate the clinical data on the risk of disease and outcomes from treatment, for the purpose of predicting risk and the value of one or another type of treatment in future patients, e.g., with information derived from the human genome project and genotyping of patients. For example, the mutation BrCa 1, which predisposes to premature breast cancer and ovarian cancer, is not a single entity. It is known already that there are 300 mutations of this gene.

The impact of each mutation—or even a single specific mutation—on the incidence or outcome of breast cancer is not known. This behavior cannot be predicted from the presence of a mutation of a given type. The clinical significance of any mutation of the BrCa 1 gene will be determined from studies of large numbers of patients for whom detailed medical histories are available independent of whether the patients carry a mutation of the gene and for whom the histories can be analyzed using the power of computing and statistics.

The purpose of such analysis, with the present invention as its basis, is to determine the specific significance of different types of genetic mutations for early onset of clinical disease and the factors that affect penetrance. Therefore, the present invention allows for the inexpensive collection and database storage of large amounts of medically significant information, across a population, that can be analyzed in light of the presence or absence of one or another type of genetic mutation that predisposes the affected individual to a disease.

For example, data for the longitudinal course of disease can be manipulated directly to account for differences in ages of onset of disease in different patients, and to compare longitudinal courses of disease as a function of age, for different ages, or to compare the longitudinal courses of disease after correction for different ages of onset in different patients. Alternatively, the data can be manipulated to compare patients vertically at any specific time in the longitudinal course of a disease, with or without automatic correction for age of onset of disease.

The data can be examined with any type of statistical program. This type of review cannot be accomplished using any current version of electronic medical records. This is so because of the electronic medical record (EMR) systems available, as compared with the present invention, do not insure the completeness or accuracy of the medical record obtained. By contrast, according to the present invention, EMRs neither decreases the use of physician or assistant's time for acquiring a medical history nor do they add to the knowledge base and logic systems (database 101, FIG. 1) for acquiring and analyzing facts as the doctor or assistant take a medical history. Moreover, the database of medical facts assembled by EMRs are easily corrupted because they allow automated insertion of answers to questions that were never asked and they allow automated insertion of results of physical findings that were not elicited. Thus, databases supplied by EMRs, as compared with the present invention are highly likely to be incomplete, inadequate, and corrupted.

2. The Current Invention Provides a New Mechanism for Monitoring the Practice Habits of Physicians The database use of the present invention makes it possible to directly monitor practice habits, monitor the need for further education of physicians or individual physicians in specific areas of practice, for population statistics on disease, and for new approaches to problems of clinical research.

For example, the database component of the present invention can be used to monitor the efficiency and adequacy of care rendered by a specific physician or group of physicians, which can be done without disturbing the confidentiality of the medical database. The medical databases for all patients in a given practice can be examined rapidly by computer-aided systems to establish a variety of parameters for efficiency and adequacy of practice. These could include, but are not limited to, the number of patients with different diseases who do or do not meet treatment goals, whether a physician uses the expert guidelines provided by the system, and so on. Such analyses can be accomplished across all patients in a practice or can be selected to identify patients with specific disease profiles. System review can be used to determine the mix of diseases in different practices. Results of practice reviews can be compared between practices or across an array of practices. This sort of critical review of medical practices is impossible at the moment if one were to rely on review of hand-written charts or even typewritten notes. Therefore, electronic medical records that are currently available will not meet the standards for this type of review.

The practice review aspect of the system and method of the present invention is especially applicable in the teaching situation where it can be used to monitor the performance of medical students and residents, and where it can be used to monitor changes in performance with increasing years of training. Thus, it can determine the value of different types of educational programs because the present invention makes it possible to measure whether one or another educational program actually enhances patient care, and how long an effect an educational program has on enhancing patient care. The review aspects of the present invention can be used, for example, to identify areas of practice in which better education of physicians is important because of general deficiencies in the efficiency and adequacy of diagnosis and treatment of specific diseases or of diseases in specific clinical settings.

The system and method of the present invention can be used to determine, on an ongoing basis, the impact of type of medical training, length of training, location of training, and so on practice habits. It can be used to determine the effect of time since training ended, age, and so on practice habits.

The present invention can be used by physicians to monitor their own experience with patients, who appear to have identical diseases. Thus, each physician with patients who use the present invention can monitor their own practice by searching the database for the files of their patients.

Physicians with patients who use the invention can also use it to organize aspects of their practices. It is possible with the present invention, for example, for physicians to group revisits of patients with the same disease for the same day, which enhances the recall of medically relevant information by the physician and which facilitates the educational process by the physician. Thus, a physician might elect to see all the diabetic patients in his/her practice on the same day of the week and to see all patients with chronic lung disease on another day of the week. Physicians can use the present invention to automatically organize their practices in this way.

Referring to FIG. 6, a system access card is shown at 600. The system access card will permit the holder to obtain general medical history information from system database 306 and educational information from database 308. It is understood that database 308 may include the information in databases 105 and 106 but it could include more or less than the information in their databases. However, the general information that system access card 600 will permit the holder to access will be of the type that does not reveal the identity of any patients to whom the information relates. As such, only anonymous medical history information may be obtained.

Referring to 7, generally at 700, a system control and storage card is shown at 750. The system control and storage ("SCS") card is used by patients for the purposes of permitting access to their particular medical record. The SCS card will relate the patient with his or her particular medical history information. Moreover, this card will permit the patient to control which physicians will be able to relate medical history and other relevant medical information with that patient. For example, if a patient desires to change primary care physicians, he or she could terminal identity access to the old physician and grant identity access to medical history information to the new physician. Moreover, the SCS card also may include a storage section that will permit the patient to store his/her entire medical history by removing it from the system of the present invention but retaining it for later download.

When a patient has information entered into the system for the first time, he/she will be given a unique identifier code under which the patient's history and related medical information will be stored. The system protects these identifier codes so that access to medical history information and the patient related to that medical history information is controlled. These is, it is inaccessible except to his/her physicians and the patient. A method of doing this would be through the use of SCS card 750 shown in FIG. 7.

The system and method of the present invention also may be configured so that a physician may be granted access only to the files and the identity of the patient for those files for that patients that are his/her patients or patients for whom he or she have been asked to consult. This method would permit the physician to input list of his/her patients rather than only on a single access basis using SCS card 750 shown in FIG. 7.

Security for the system of the present invention controls access to the constructed medical histories of patients with the identity of the patients. If a physician does not have the proper access availability he/she will be denied access to identity information. Accordingly, the security of the system will allow or deny access to specific physicians in the event the patient changes physicians, HMOs, or a second medical opinion. Therefore, a patient, through use of security codes, may grant a new physician permission to examine his/her particular past medical history and the system will also permit that physician to retrieve pertinent continuing medical education materials that apply to the patient's specific problem, while at the same time denying the patient's former physician access to his or her medical history.

Medical history information that is entered into the file of a particular patient is time-stamped to make it possible to reconstruct the exact sequence of all events that are/were medically relevant during the diagnostic and therapeutic phases of medical care. This will provide the physician with the information in the way that it is normally provided. As such, the physician who is in charge of the patient's care on any given day will have the pertinent information available so that the most informed decisions about the patient's care may be made.

The terms and expressions that are employed herein are terms or description and not of limitation. There is no intention in the use of such terms and expressions of excluding the equivalents of the feature shown or described, or portions thereof, it being recognized that various modifications are possible within the scope of the invention as claimed.

I claim:
1. A computer-implemented method for acquiring and evaluating patient information, comprising the steps of:
   (a) querying a patient regarding conditions of the patient's health including symptoms and other indicia of disease or illness and processing input data that is based on responses to queries at step (a), and generating a chief complaint based on the responses to the queries and a medical history for the patient;
   (b) rule-based searching with a computer the input data in the medical history for predetermined medically significant words and phrases, and generating a set of preliminary diagnoses based on the chief complaint and the identified medically significant words and phrases;
   (c) rule-based searching with a computer the input data in the medical history for characteristic of the patient for a likelihood of each preliminary diagnosis generated in step (b) and generating a set of working diagnoses based on a predetermined likelihood of occurance value;
   (d) selecting a set of preliminary working diagnosis from the set of working diagnoses generated at step (c) based on predetermined criteria;
   (e) retrieving specific, relevant historical and up-to-date information relating to each working diagnosis of the set of preliminary working diagnoses;
   (f) rule-based searching with a computer of the input data in the medical history for predetermined quality of pain words and phrases, matching identified quality of pain words and phrases with the selected set of preliminary working diagnosis selected by steps (d), and generating a second set of preliminary working diagnoses based on matching identified words and phrases with the selected set of preliminary working diagnosis;
   (g) querying the patient as to one or more locations of pain and processing input data based on responses to the queries at step (g);
   (h) generating a second set of preliminary working diagnosis based on the input data according to the responses to the queries at step (g);
   (i) generating a list of differential diagnoses based on the second set of preliminary working diagnoses;
   (j) querying the patient as to risk information associated with the differential diagnoses and processing input data based on responses to the queries at step (j);
   (k) rule-based searching with a computer for guidelines based on the medical history and evaluating the differential diagnoses to confirm or exclude differential diagnoses from the list of differential diagnoses;
   (l) rule-based searching with a computer for treating the differential diagnoses confirmed at step (k); and
   (m) generating a report for a physician of a final diagnosis based on the confirmed differential diagnoses and including as part of the report the retrieved specific, relevant historical and up-to-date information at step (e) refined for the confirmed differential diagnoses.

2. The method as recited in claim 1, wherein the querying at step (a) includes querying an anatomical location of disease or illness for the chief complaint.

3. The method as recited in claim 2, wherein the generated preliminary diagnoses are based on the anatomical location of disease or illness for the chief complaint.

4. The method as recited in claim 1, wherein the method continuously evaluates the input data at steps (a), (g), and (j) in the medical history to determine if the selected set of preliminary working diagnosis selected at step (d), the second set of preliminary working diagnosis at step (h), or the list of differential diagnoses, respectively, are diagnoses upon which the method is to proceed.

5. The method as recited in claim 1, wherein the risk information includes patient habit information.

6. The method as recited in claim 1, wherein the risk information includes patient medication use.

7. The method as recited in claim 6, wherein the method evaluates the compatibility of the use of a plurality of medications.

8. A computer-implemented method for acquiring and evaluating patient information, comprising the steps of:
- (a) querying a patient regarding conditions of the patient's health including symptoms and other indicia of disease or illness and processing input data that is based on responses to queries at step (a), and generating a chief complaint based on the responses to the queries and a medical history for the patient;
- (b) rule-based searching with a computer the input data in the medical history for predetermined medically significant words and phrases, and generating a set of preliminary diagnoses based on the chief complaint and the identified medically significant words and phrases;
- (c) rule-based searching with a computer the input data in the medical history for characteristic of the patient for a likelihood of each preliminary diagnosis generated in step (b) and generating a set of working diagnoses based on a predetermined likelihood of occurance value;
- (d) selecting a set of preliminary working diagnosis from the set of working diagnoses generated at step (c) based on predetermined criteria;
- (e) retrieving specific, relevant historical and up-to-date information relating to each working diagnosis of the set of preliminary working diagnoses;
- (f) rule-based searching with a computer of the input data in the medical history for predetermined quality of pain words and phrases, matching identified quality of pain words and phrases with the selected set of preliminary working diagnosis selected by steps (d), and generating a second set of preliminary working diagnoses based on matching identified words and phrases with the selected set of preliminary working diagnosis;
- (g) querying the patient as to one or more locations of pain and processing input data based on responses to the queries at step (g);
- (h) generating a second set of preliminary working diagnosis based on the input data according to the responses to the queries at step (g);
- (i) generating a list of differential diagnoses based on the second set of preliminary working diagnoses;
- (j) querying the patient as to risk information associated with the differential diagnoses and processing input data based on responses to the queries at step (j);
- (k) rule-based searching with a computer for guidelines based on the medical history and evaluating the differential diagnoses to confirm or exclude differential diagnoses from the list of differential diagnoses;
- (l) rule-based searching with a computer for treating the differential diagnoses confirmed at step (k);
- (m) generating a report for a physician of a final diagnosis based on the confirmed differential diagnoses and including as part of the report the retrieved specific, relevant historical and up-to-date information at step (e) refined for the confirmed differential diagnoses; and
- (n) generating a report for patient of a final diagnosis based on the confirmed differential diagnoses and including as part of the report the retrieved specific, relevant historical and up-to-date information at step (e) refined for the confirmed differential diagnoses and refined for patient understanding.

9. The method as recited in claim 8, wherein the querying at step (a) includes querying an anatomical location of disease or illness for the chief complaint.

10. The method as recited in claim 9, wherein the generated preliminary diagnoses are based on the anatomical location of disease or illness for the chief complaint.

11. The method as recited in claim 8, wherein the method continuously evaluates the input data at steps (a), (g), and (j) in the medical history to determine if the selected set of preliminary working diagnosis selected at step (d), the second set of preliminary working diagnosis at step (h), or the list of differential diagnoses, respectively, are diagnoses upon which the method is to proceed.

12. The method as recited in claim 8, wherein the risk information includes patient habit information.

13. The method as recited in claim 8, wherein the risk information includes patient medication use.

14. The method as recited in claim 13, wherein the method evaluates the compatibility of the use of a plurality of medications.

15. A computer-implemented method for inputting, acquiring and evaluating patient information, comprising the steps of:
- (a) querying a patient regarding conditions of the patient's health using principles of pathophysiology that are compatible with a disease condition consistent with the patient's specific responses to the queries, with the principles of pathophysiology including simulating at least logical processes for obtaining a medical history using up-to-date knowledge of disease, disease diagnoses, and disease treatment;
- (b) the inputting data to a computer regarding the patient based on responses to the queries at step (a);
- (c) acquiring a medical history for the patient including a medical history acquired using at least principles of pathophysiology;
- (d) inputting to the computer the medical history acquired at step (c);
- (e) generating with the computer in an automated manner a chief complaint for the patient, with generating the chief complaint including at least rule-based searching the responses to the queries input at step (b) and the medical history input at step (d) to at least determine medical problems and conditions that may affect management of any medical problem identified;
- (f) generating with the computer in an automated manner a set of preliminary diagnoses according to one of the substeps of;
  - (1) generating the set of preliminary diagnoses based only on the chief complaint generated at step (e) or
  - (2) generating the set of preliminary diagnoses based on the chief complaint generated at step (e) and rule-based searching with a computer the medical history input at step (d) for predetermined medically significant words and phrases if the chief complaint alone is insufficient to generate the set of preliminary diagnoses;

(g) rule-based searching with a computer in an automated manner the medical history input at step (d) for characteristics of the patient for a likelihood of each preliminary diagnosis generated in step (f) and generating in an automated manner with a computer a set of working diagnoses based on a predetermined likelihood of occurrence value;

(h) selecting with a computer a set of preliminary working diagnoses from the set of working diagnoses generated at step (g) based on predetermined criteria;

(i) retrieving in an automated manner from at least a first source other than the medical history, specific, relevant and up-to-date medical information relating to each working diagnosis of the set of preliminary working diagnoses;

(j) rule-based searching with a computer in an automated manner the input data in the medical history for predetermined quality of pain words and phrases, matching identified quality of pain words and phrases with the selected set of preliminary working diagnosis selected by steps (h), and generating with a computer in an automated manner a second set of preliminary working diagnoses based on matching identified words and phrases with the selected set of preliminary working diagnosis;

(k) querying the patient as to one or more locations of pain and processing input data based on responses to the queries at step (k);

(l) generating with a computer in an automated manner a refined second set of preliminary working diagnosis based on the input data according to the responses to the queries at step (k); and (m) generating with a computer in an automated manner a list of differential diagnoses based on the refined second set of preliminary working diagnoses;

(n) querying to obtain patient risk information associated with the differential diagnoses and processing with a computer input data based on responses to the queries at step (n);

(o) rule-based searching with a computer in an automated manner according to principles of pathophysiology at least the first source of relevant and up-to-date of medical information for guidelines to manage at least each differential diagnosis and associated risk based on the differential diagnoses identified in analyzing the medical history and evaluating with a computer the differential diagnoses to confirm or exclude differential diagnoses from the list of differential diagnoses;

(p) rule-based searching with a computer in an automated manner for treating the differential diagnoses confirmed at step (o); and (q) generating with a computer in an automated manner a report for a physician of a problem-based solution in a form of at least a set of possible diagnoses based on the confirmed differential diagnoses and including as part of the report specific, relevant and up-to-date information retrieved from at least one source other than the medical history at step (i) refined for the confirmed differential diagnoses.

* * * * *